US012564588B2

(12) United States Patent
Kiyokawa et al.

(10) Patent No.: US 12,564,588 B2
(45) Date of Patent: Mar. 3, 2026

(54) HECT E3 UBIQUITIN LIAGASE INHIBITORS AND USES THEREOF

(71) Applicant: Northwestern University, Evanston, IL (US)

(72) Inventors: Hiroaki Kiyokawa, Evanston, IL (US); Rama K. Mishra, Evanston, IL (US); Chi-Hao Luan, Evanston, IL (US)

(73) Assignee: Northwestern University, Evanston, IL (US)

( * ) Notice: Subject to any disclaimer, the term of this patent is extended or adjusted under 35 U.S.C. 154(b) by 405 days.

(21) Appl. No.: 18/261,778

(22) PCT Filed: Jan. 21, 2022

(86) PCT No.: PCT/US2022/013257
§ 371 (c)(1),
(2) Date: Jul. 17, 2023

(87) PCT Pub. No.: WO2022/159666
PCT Pub. Date: Jul. 28, 2022

(65) Prior Publication Data
US 2024/0091219 A1 Mar. 21, 2024

Related U.S. Application Data

(60) Provisional application No. 63/200,239, filed on Feb. 24, 2021, provisional application No. 63/140,077, filed on Jan. 21, 2021.

(51) Int. Cl.
*A61K 31/496* (2006.01)
*A61P 35/00* (2006.01)

(52) U.S. Cl.
CPC ............ *A61K 31/496* (2013.01); *A61P 35/00* (2018.01)

(58) Field of Classification Search
None
See application file for complete search history.

(56) References Cited

U.S. PATENT DOCUMENTS 9,725,708 B2 8/2017 Haas et al.

FOREIGN PATENT DOCUMENTS

WO WO-2020247860 A1 * 12/2020 ........... C07D 401/12
WO WO-2022120207 A1 * 6/2022 ........... C07C 237/42

OTHER PUBLICATIONS

Weston et al., The SKI complex is a broad-spectrum, host-directed antiviral drug target for coronaviruses, influenza, and filoviruses, Proc. Natl. Acad. Sci. U.S.A. 117 (48) 30687-30698 (Year: 2020).*

(Continued)

*Primary Examiner* — Jeffrey S Lundgren
*Assistant Examiner* — Anthony Joseph Seitz
(74) *Attorney, Agent, or Firm* — Quarles & Brady LLP

(57) ABSTRACT

Disclosed herein are compounds, compositions, and methods for inhibiting HECT E3 ubiquitin ligases. In some embodiments, the compounds are formulated as a pharmaceutical composition and administered to a subject in need thereof. In some embodiments, the subject in need thereof is diagnosed with a neurological disease or a cancer characterized by increased or ectopic HECT E3 ligase activity.

12 Claims, 8 Drawing Sheets

Specification includes a Sequence Listing.

(56) References Cited

OTHER PUBLICATIONS

Wadood et al., (2012), A Novel Pharmacophore Model to Identify Leads for Simultaneous Inhibition of Anti-coagulation and Anti-inflammatory Activities of Snake Venom Phospholipase A2. Chemical Biology & Drug Design, 79: 431-441 (Year: 2012).*
International Search Report, corresponding to PCT/US22/13257, dated Apr. 28, 2022.
Babu, U., et al., "*Salmonella enteritidis* clearance and immune responses in chickens following Salmonella vaccination and challenge," Vet. Immunol. Immunopathol. (2004) 101:251-257.
Huang, L., Kinnucan, E., Wang, G., Beaudenon, S., Howley, P. M., Huibregtse, J. M., and Pavletich, N. P. (1999) Structure of an E6AP-UbcH7 complex: insights into ubiquitination by the E2-E3 enzyme cascade. Science 286, 1321-1326.
Owais, A., Mishra, R. K., and Kiyokawa, H. (2020) The HECT E3 Ligase E6AP/UBE3A as a Therapeutic Target in Cancer and Neurological Disorders. Cancers (Basel) 12, 2108.
Hopkins, A. L., and Groom, C. R. (2002) The druggable genome. Nat Rev Drug Discov 1, 727-730.
Cheng, A. C., Coleman, R. G., Smyth, K. T., Cao, Q., Soulard, P., Caffrey, D. R., Salzberg, A. C., and Huang, E. S. (2007) Structure-based maximal affinity model predicts small-molecule druggability. Nat Biotechnol 25, 71-75.
Halgren, T. A. (2009) Identifying and characterizing binding sites and assessing druggability. J Chem Inf Model 49, 377-389.
Loving, K. A., Lin, A., and Cheng, A. C. (2014) Structure-based druggability assessment of the mammalian structural proteome with inclusion of light protein flexibility. PLoS Comput Biol 10, e1003741.
Jordan, J. B., Poppe, L., Xia, X., Cheng, A. C., Sun, Y., Michelsen, K., Eastwood, H., Schnier, P. D., Nixey, T., and Zhong, W. (2012) Fragment based drug discovery: practical implementation based on (1)(9)F NMR spectroscopy. J Med Chem 55, 678-687.
Sterling, T., and Irwin, J. J. (2015) ZINC 15—Ligand Discovery for Everyone. J Chem Inf Model 55, 2324-2337.
Lipinski, C. A. (2004) Lead- and drug-like compounds: the rule-of-five revolution. Drug Discov Today Technol 1, 337-341.
Wan-Mamat, W. M., Isa, N. A., Wahab, H. A., and Wan-Mamat, W. M. (2009) Drug-like and non drug-like pattern classification based on simple topology descriptor using hybrid neural network. Conf Proc IEEE Eng Med Biol Soc 2009, 6424-6427.
Baell, J. B., and Holloway, G. A. (2010) New substructure filters for removal of pan assay interference compounds (PAINS) from screening libraries and for their exclusion in bioassays. J Med Chem 53, 2719-2740.
Mishra, R. K., and Singh, J. (2015) A Structure Guided QSAR: A Rapid and Accurate technique to predict IC50: A Case Study. Curr Comput Aided Drug Des 11, 152-163.
Mishra, R. K., Shum, A. K., Platanias, L. C., Miller, R. J., and Schiltz, G. E. (2016) Discovery and characterization of novel small-molecule CXCR4 receptor agonists and antagonists. Sci Rep 6, 30155.
Klionsky, D. J., Abdelmohsen, K., Abe, A., Abedin, M. J., Abeliovich, H., Acevedo Arozena, A., Adachi, H., Adams, C. M., Adams, P. D., Adeli, K., Adhihetty, P. J., Adler, S. G., Agam, G., Agarwal, R., Aghi, M. K., et al. (2016) Guidelines for the use and interpretation of assays for monitoring autophagy (3rd edition). Autophagy 12, 1-222.
Villa, S. R., Mishra, R. K., Zapater, J. L., Priyadarshini, M., Gilchrist, A., Mancebo, H., Schiltz, G. E., and Layden, B. T. (2017) Homology modeling of FFA2 identifies novel agonists that potentiate insulin secretion. J Investig Med 65, 1116-1124.
Sherman, W., Day, T., Jacobson, M. P., Friesner, R. A., and Farid, R. (2006) Novel procedure for modeling ligand/receptor induced fit effects. J Med Chem 49, 534-553.
Verdonk, M. L., Chessari, G., Cole, J. C., Hartshorn, M. J., Murray, C. W., Nissink, J. W., Taylor, R. D., and Taylor, R. (2005) Modeling water molecules in protein-ligand docking using Gold. J Med Chem 48, 6504-6515.
Jain, A. N. (2003) Surflex: fully automatic flexible molecular docking using a molecular similarity-based search engine. J Med Chem 46, 499-511.
Wang, Y., Liu, X., Duong, D. M., Bhuripanyo, K., Zhao, B., Bi, Y., Kiyokawa, H., and Yin, J. (2017) Indentifying the ubiquitination targets of E6AP by Orthogonal Uniquitin Transfer. Nature Communications 8, 2232.
Yamagishi, et al., Chem Biol. Dec. 23, 2011;18(12):1562-70 (PMID:22195558).
Cherry et al., PLoS One. Dec. 23, 2013;8(12):e84506. doi: 10.1371/journal.pone.0084506. eCollection 2013 (PMID: 24376816).
Ricci-Lopez et al., PLoS One Mar. 15, 2019;14(3):e0213028. doi: 10.1371/journal. pone.0213028. eCollection 2019 (PMID: 30875378).
Beerheide, et al., J Natl Cancer Inst. Jul. 21, 1999;91(14):1211-20. doi: 10.1093/jnci/ 91.14.1211 (PMID: 10413422).
Ronchi, et al., J Biol Chem Jan. 10, 2014;289(2):1033-48. doi: 10.1074/jbc. M113.517805. Epub Nov. 22, 2013 (PMID: 24273172).
Kirov, et al., Biol Psychiatry Mar. 1, 2014;75(5):378-85. doi: 10.1016/j.biopsych. 2013.07.022. Epub Aug. 28, 2013 (PMID: 23992924).
Depienne et al., Biol Psychiatry . Aug. 15, 2009;66(4):349-59. doi: 10.1016/j.biopsych. 2009.01.025. Epub Mar. 17, 2009 (PMID: 19278672).
Malhortra, et al., Cell Mar. 16, 2012;148(6): 1223-41. doi:10.1016/j.cell.2012.02.039. (PMID: 22424231).
De-luca et al., Mol Psychiatry Oct. 2013; 18(10):1090-5. doi: 10.1038/mp.2012. 138. Epub Oct. 9, 2012 (PMID:23044707).
Hershko, et al., Annu. Rev. Biochem., 1998 67, 425.
Lee et al., Cell, 2008, 134, 268.
Wenzel et al., Biochem. J. 2011, 433, 31.
Hatakeyama et al., Biochem. Biophyx. Res. Commun. 2003, 302, 635.
Deshaies, et al., Annu. Rev. Biochem., 2009, 78, 399.
Rotin et al., Nat. Rev. Mol. Cell Biol. 2009, 10, 398.
Jin et al., Dual E1 activation systems for ubiquitin differentially regulate E2 enzyme charging. Nature. 447, 1135-1138 (2007).
Weber et al., Front. Physiol., Apr. 3, 2019.
Schulman et al., Ubiquitin-like protein activation by E1 enzymes: the apex for downstream signaling pathways. Nat. Rev. Mol. Cell Biol. 10, 319-331 (2009).
Medvar et al., Comprehensive database of human E3 ubiquitin ligases: application to aquaporin-2 regulation. Physiol Genomics 2016; 48(7)502-512.
Li X, Elmira E, Rohondia S, Wang J, Liu J, Dou QP. A patent review of the ubiquitin ligase system: 2015-2018. Expert Opin Ther Pat. Dec. 2018;28(12):919-937. doi: 10.1080/13543776.2018.1549229. Epub Nov. 23, 2018. PMID: 30449221; PMCID: PMC6398165.

* cited by examiner

Figure 3A-B
A
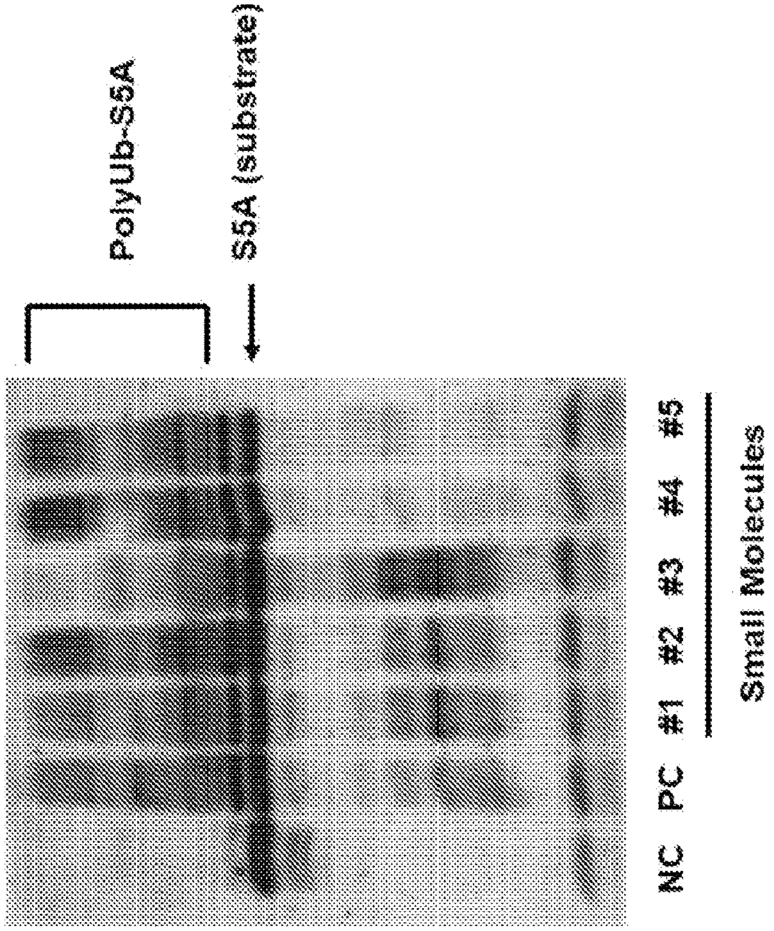
B
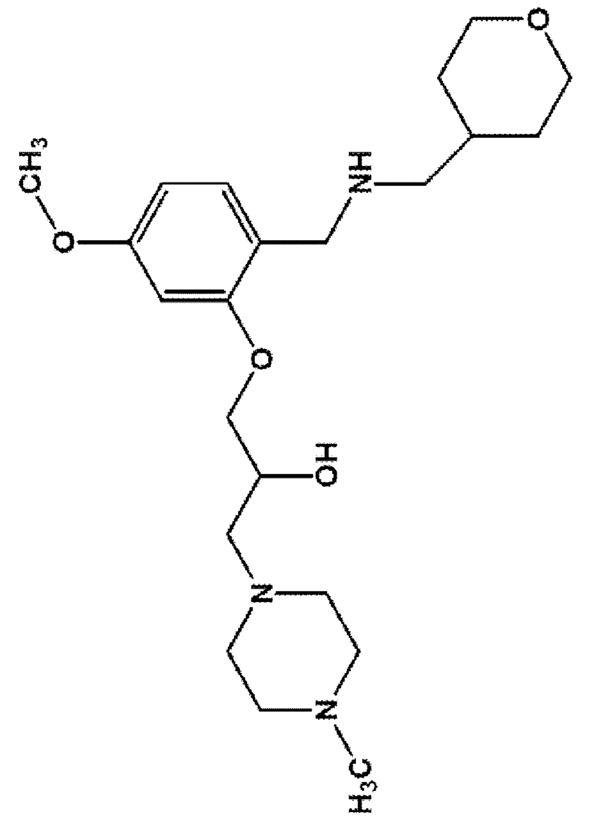

Figure 4A-B
A
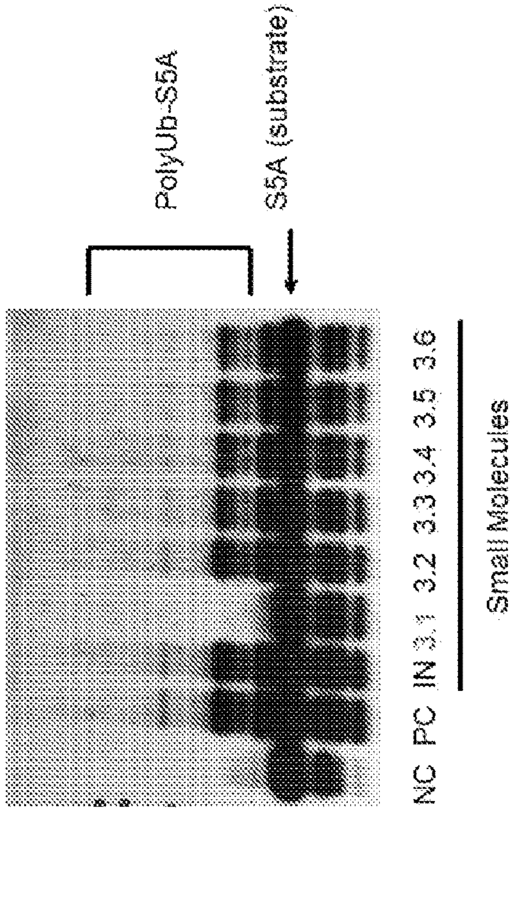
B
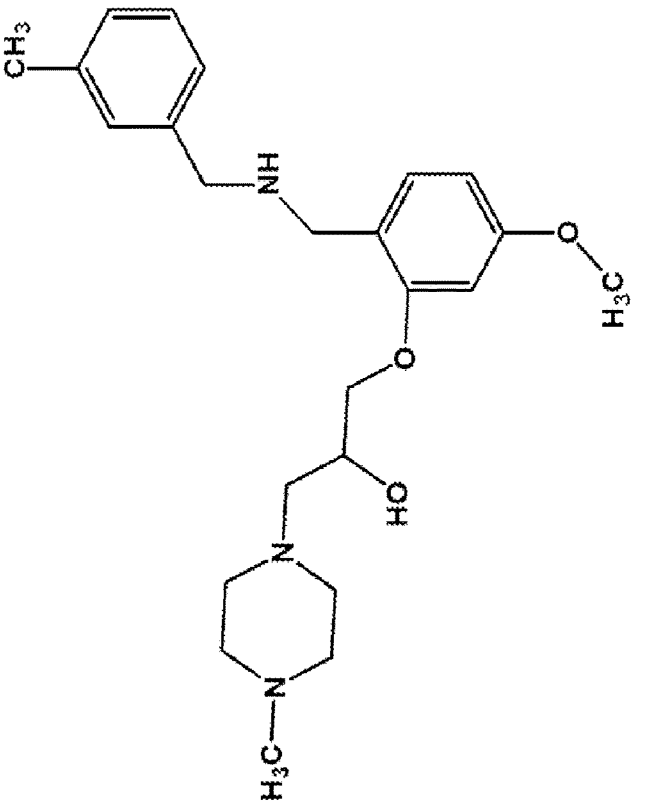

Figure 5A-B
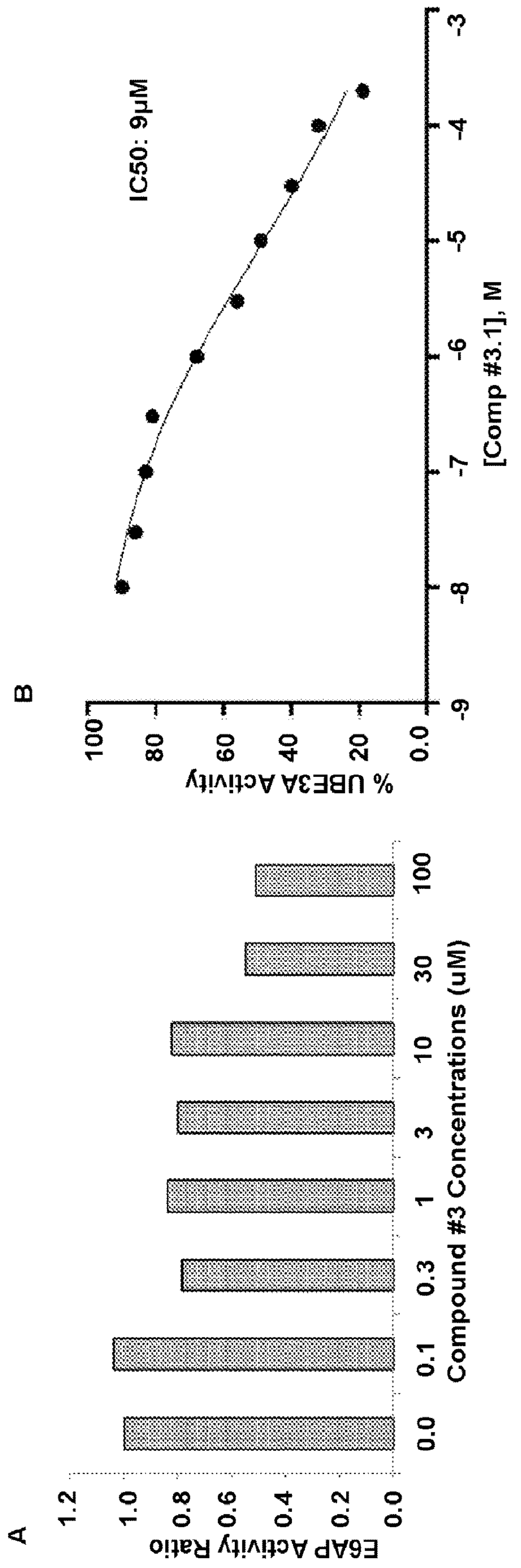

Figure 6A-B
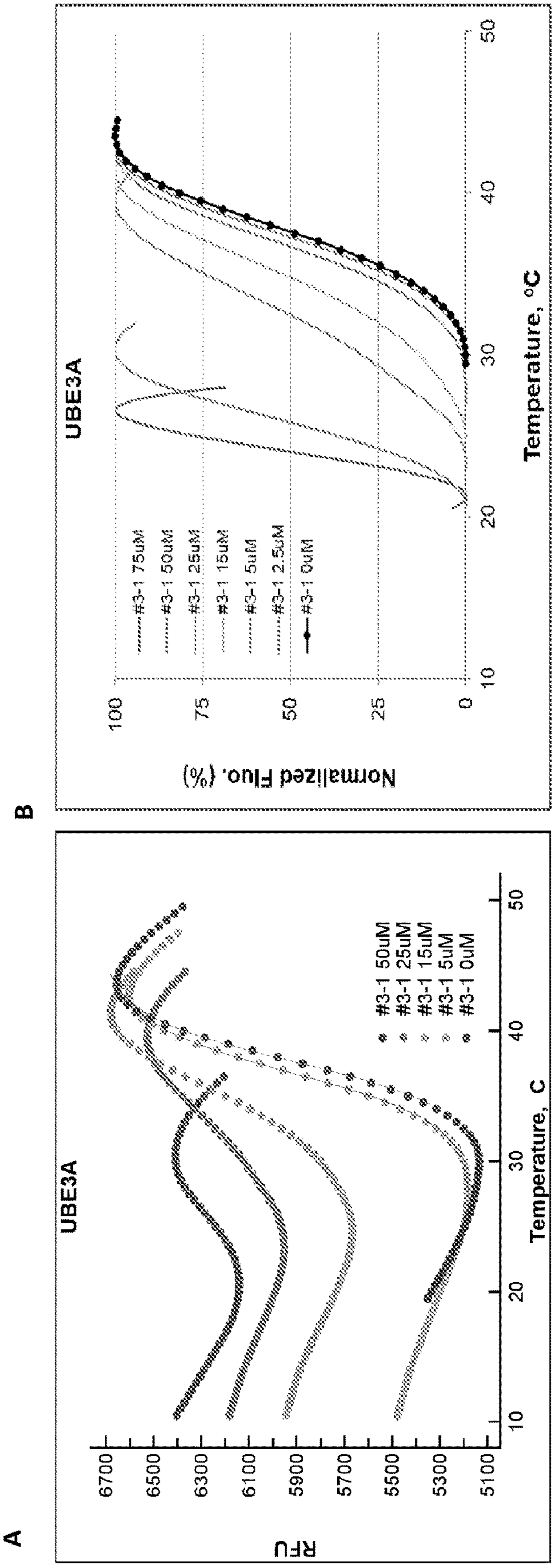

HECT E3 UBIQUITIN LIAGASE INHIBITORS AND USES THEREOF

CROSS-REFERENCE TO RELATED APPLICATIONS

This application is the U.S. National Stage of PCT/US2022/013257 with international filing date of Jan. 21, 2022, which claims the benefit of U.S. Provisional Application No. 63/140,077 filed Jan. 21, 2021, and U.S. 63/200,239 filed Feb. 24, 2021. The entire content of the above-referenced applications is incorporated herein by reference.

SEQUENCE LISTING

A Sequence Listing accompanies this application and is submitted as an ASCII text file of the sequence listing named "702581_02093_ST25.txt" which is 29,372 bytes in size and was created on Jan. 20, 2022. The sequence listing is electronically submitted via EFS-Web with the application and is incorporated herein by reference in its entirety.

BACKGROUND

The E1-E2-E3 enzymatic cascades are known in the art to mediate ubiquitin (UB) transfer and they constitute a key part of cell signaling networks. (See, e.g., Hershko, et al., *Annu. Rev. Biochem.,* 1998 67, 425, the content of which is incorporated herein by reference in its entirety). In E1-E2-E3 cascades, E1 first activates UB to form a UB~E1 thioester conjugate with the C-terminal carboxylate of UB bonded to a catalytic Cys residue of E1. (See, e.g., Lee et al., *Cell,* 2008, 134, 268, the content of which is incorporated herein by reference in its entirety). Next, UB is transferred to a catalytic Cys residue on E2 to form a UB~E2 conjugate. Subsequently, E2 carries UB to an E3 that recruits substrate proteins and catalyzes isopeptide bond formation between the C-terminal Gly of UB and Lys residues on the substrates. (See, e.g., Wenzel et al., *Biochem. J.* 2011, 433, 31; the content of which is incorporated by reference in its entirety). Several hundred E3s are known, and E3s are classified into 28 HECT, 7 U-box, 12 RBR, and more than 600 Ring types based on the domain structures to engage the UB~E2 conjugate. (See, e.g., Deshaies, et al., *Annu. Rev. Biochem.,* 2009, 78, 399; Hatakeyama et al., *Biochem. Biophyx. Res. Commun.* 2003, 302, 635; and Rotin et al., *Nat. Rev. Mol. Cell Biol.* 2009, 10, 398; the contents of which are incorporated by reference in their entireties). HECT and RBR E3s rely on a catalytic Cys residue to uptake UB from an E2 before transferring UB to the substrates. U-box and Ring E3s directly transfer UB from E2 to the substrates.

One of the HECT E3 ligases, E6AP, which is also known as UBE3A, plays roles in oncogenesis, neurodevelopmental disorders, and other human diseases. The UBE3A gene is located at the chromosome region 15q11-13 and encodes a HECT-type ubiquitin ligase UBE3A/E6AP. UBE3A plays important roles not only in brain development but also in viral and non-viral carcinogenesis. Duplication or triplication of 15q11-13 (Dup15q syndrome) renders individuals highly susceptible to autism spectrum disorders (ASD). Indeed, Dup15q is one of the most common cytogenetic anomalies in ASD cohorts. Studies using mouse models of Dup15q suggest that overexpression of UBE3A in neurons accounts for most of the ASD phenotype. It is thought that neurons in developing brain requires proper control of the ubiquitin ligase activity of UBE3A, and excess UBE3A activity could perturb synaptic networks leading to autistic traits.

Excess or ectopic activity of UBE3A could also drive cancer development. The E6 oncoprotein encoded by human papillomavirus (HPV) binds and facilitates UBE3A to ubiquitinate tumor suppressor proteins such as p53 and p27, thus leading to the development of cervical cancer and head/neck cancer.

Although pharmacological inhibition of UBE3A is perceived to be a reasonable therapeutic strategy to suppress or alleviate autistic symptoms in children with Dup15q and/or to block progression of the HPV-induced cancers, no such agent has been available. Accordingly, there is a need in the art for HECT E3 ligase inhibitors.

SUMMARY

Disclosed herein are compounds, compositions, and methods useful for treating diseases and conditions characterized by increased activity and/or expression of HECT E3 ligases in a subject in need thereof. In some embodiments, the compound comprises Formula I, Formula II, Formula III, a derivative, isomer, or a pharmaceutically acceptable salt thereof, or a combination thereof, and in some embodiments, the compound is formulated as a pharmaceutical composition. In some embodiments, the HECT E3 ligase comprises UBE3A.

In some embodiments, a subject in need thereof is suffering from, diagnosed with, or suspected of having a neurological disorder or a cancer.

In some embodiments, the cancer is one or more of HPV associated cancer (e.g., HPV-induced cervical, skin and head/neck cancers); HCV associated cancer (e.g., liver cancer), cancer characterized by PML downregulation (e.g., Burkitt's lymphoma and prostate cancer), non-small cell lung cancer, and breast cancer.

In some embodiments, the neurological disorder is one or more of Angelman syndrome (AS), Autism Spectrum Disorders (ASD), and chromosome 15q11.2-q13.3 duplication syndrome (Dup15q).

BRIEF DESCRIPTION OF THE FIGURES

FIG. 3A-B. Identification of a potential UBE3A inhibitor compound by in vitro ubiquitination assay. (A). Purified UBA1 (E1), UBE2L3 (E2) and UBE3A (E3) were pre-incubated with each compound at 100 uM, followed by incubation with purified ubiquitin (Ub) and S5A in the presence of ATP. UBE3A-mediated polyubiquitination of S5A is shown as poly Ub-S5A. #3 inhibited formation of PolyUb-S5A. NC, negative control without active UBE3A; PC, positive control with active UBE3A but with no small molecule. (B). Structure of #3 compound (Zinc 23375107).

FIG. 4A-B. Screening for compounds that are structurally analogous to #3 compound and could bind to the druggable hotspot of the UBE3A HECT domain. Left panel (A): Purified UBA1 (E1), UBE2L3 (E2) and UBE3A (E3) were pre-incubated with structural analogs of #3 compound at 100 μM, followed by incubation with purified ubiquitin (Ub) and S5A in the presence of ATP. UBE3A-mediated polyubiquitination of S5A is shown as poly Ub-S5A. #3.1 inhibited formation of PolyUb-S5A. NC, negative control without active UBE3A; PC, positive control with active UBE3A but with no small molecule; IN an inactive small molecule. Right panel (B): Structure of #3-1 compound (1-(5-methoxy-2-{[(3-methylbenzyl)amino]methyl}phenoxy)-3-(4-methyl-1-piperazinyl) -2-propanol), which showed significant inhibition of UBE3A-mediated polyubiquitination of S5A.

FIG. 5A-B. Inhibition of the E3 activity of UBE3A by various concentrations of compound #3 and #3-1. The UBE3A activity was assayed by the in vitro ubiquitination assay using S5A as a substrate and the indicated concentrations of compound #3 (A) or #3-1 (B). The polyubiquitinated forms of S5A were quantified by western analysis.

FIG. 6A-B. Fluorescence thermal shift analysis of recombinant UBE3A HECT domain with the compound #3-1. (A) Melting curves of recombinant UBE3A HECT domain with multiple concentrations of #3-1 show the melting temperature Tm was shifted to lower temperature progressively with increase in #3-1 concentration. The rise of pre-transition background reading indicates destabilizing of the protein by the small molecule inhibitor, which is consists with the decrease of Tm by the compound. (B) Plot of normalized melting curves with respect to compound concentrations. The compound #3-1 shifts the melting temperature in a significant fashion, indicating specific binding. For example, the Tm is shifted 2.5 degree by 15 uM #3-1 and 5.1 degree by 25 uM #3-1 from the reference value. The test was done with 0.5 uM UBE3A in Hepes buffer (20 mM Hepes, 150 mM NaCl, pH7.5).

DETAILED DESCRIPTION

Figure 1:
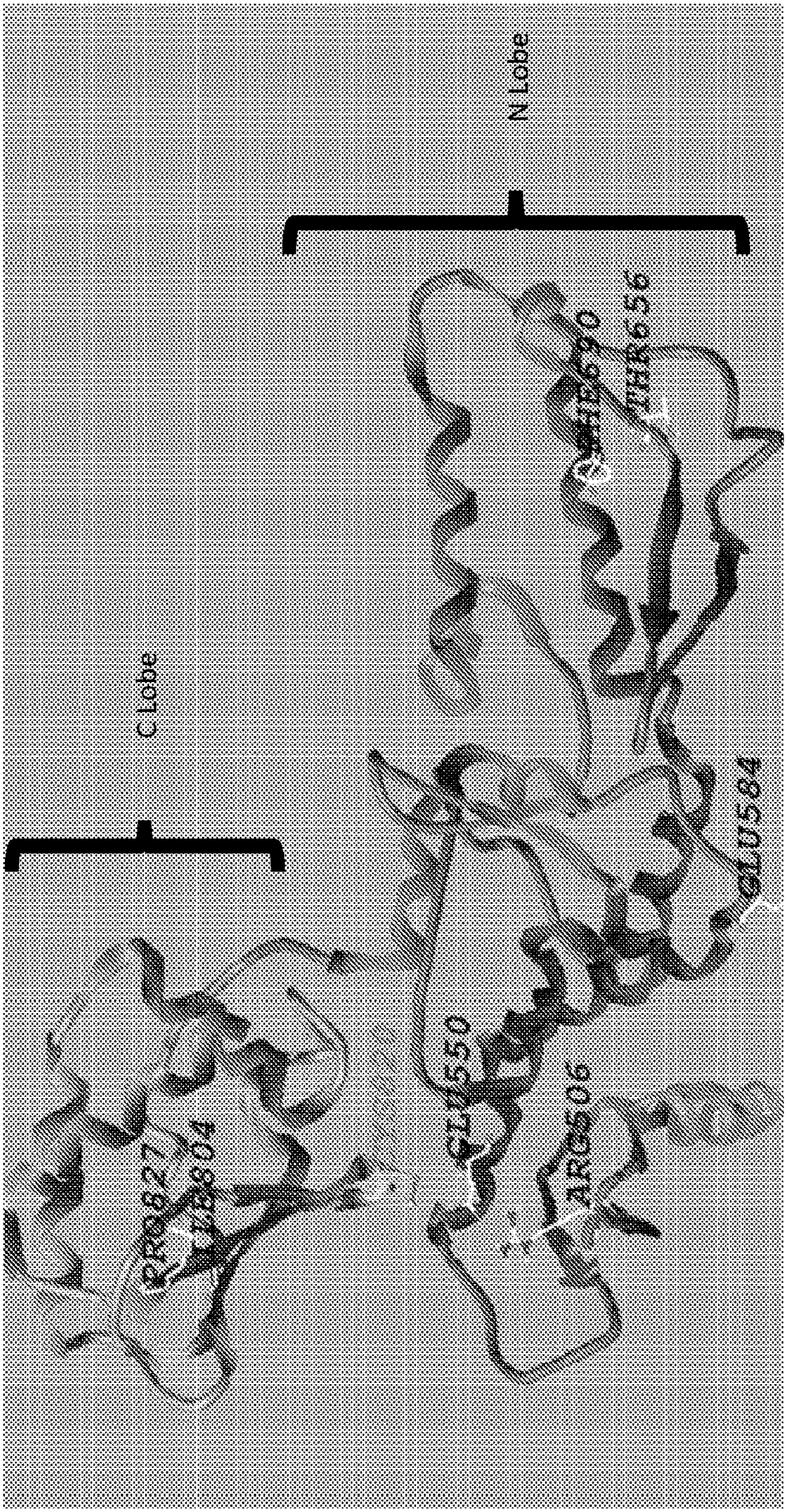
FIG. 1. The structure of the UBE3A HECT domain. The N lobe is colored in magenta (lower ⅔ of the structure) and the C lobe is colored in green (upper ⅓ of the structure). The catalytic Cys820 is labeled in red. Hereditary and de novo missense mutations found in the indicated amino acids are thought to be pathogenic in Angelman syndrome (AS) patients. The Biopolymer module of Tripos software was used to generate the figure, considering the E6AP part of 1C4z.pdb crystal structure (2).

We have screened a library of purchasable small molecule compounds, associated with ZINC (zinc.docking.org), for inhibitors of the ubiquitin ligase activity of UBE3A and identified two compounds that inhibit UBE3A-mediated ubiquitination of S5A, a known UBE3A substrate. In addition to the therapeutic use of these compounds as UBE3A inhibitors, these chemicals will also be used as lead compounds for further development of potent drugs that target UBE3A, and which would have broad-spectrum applications in clinic.

The present invention is described herein using several definitions, as set forth below and throughout the application.

Definitions and Terminology

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a component" should be interpreted to mean "one or more components" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into subranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

Polynucleotides and Uses Thereof

The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

The terms "nucleic acid" and "oligonucleotide," as used herein, may refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, *E. coli*, plants, and other host cells.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

Peptides, Polypeptides, and Proteins

As used herein, the terms "protein" or "polypeptide" or "peptide" may be used interchangeable to refer to a polymer of amino acids. Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids.

A "protein" as contemplated herein typically comprises a polymer of naturally or non-naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, polysialylation (e.g., the addition of polysialic acid), glypiation (e.g., glycosylphosphatidylinositol (GPI) anchor formation), hydroxylation, iodination (e.g., of thyroid hormones), and phosphorylation (e.g., the addition of a phosphate group, usually to serine, tyrosine, threonine or histidine).

The proteins disclosed herein may include "wild type" proteins and variants, mutants, and derivatives thereof. As used herein the term "wild type" is a term of the art understood by skilled persons and means the typical form of an organism, strain, gene or characteristic as it occurs in nature as distinguished from mutant or variant forms. As used herein, a "variant, "mutant," or "derivative" refers to a protein molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a mutant or variant molecule may have one or more insertions, deletions, or substitution of at least one amino acid residue relative to a reference polypeptide.

Regarding proteins, a "deletion" refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide). A "variant," "mutant," or "derivative" of a reference polypeptide sequence may include a deletion relative to the reference polypeptide sequence.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full-length polypeptide. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide.

The following table provides a list of exemplary conservative amino acid substitutions which are contemplated herein:

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

As used herein, the term "subject" may be used interchangeably with the term "patient" or "individual" and may include an "animal" and in particular a "mammal." Mammalian subjects may include humans and other primates, domestic animals, farm animals, and companion animals such as dogs, cats, guinea pigs, rabbits, rats, mice, horses, cattle, cows, and the like.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

As used herein "control," as in "control subject" or "control sample" has its ordinary meaning in the art, and refers to a sample, or a subject, that is appropriately matched to the test subject or test sample and is treated or not treated as appropriate.

A "therapeutic agent" or "therapeutic molecule" includes a compound or molecule that, when present in an effective amount, produces a desired therapeutic effect, pharmacologic and/or physiologic effect on a subject in need thereof. It includes any compound, e.g., a small molecule drug, or a biologic (e.g., a polypeptide drug or a nucleic acid drug) that when administered to a subject has a measurable or conveyable effect on the subject, e.g., it alleviates or decreases a symptom of a disease, disorder or condition.

As used herein the term "inhibit" or "inhibiting" with respect to the activity of a protein or enzyme (e.g., a HECT E3 ligase) refers to lessening, decreasing, or completely blocking or preventing a measurable activity. Inhibition may be permanent as to a specific molecule, or may be temporary, for example, inhibition may be reversible.

Ubiquitin

The ubiquitin protein is known in the art. (See, e.g., Herschko et al., The ubiquitin system. *Annu. Rev. Biochem.* 67, 425-479 (1998), the content of which is incorporated herein by reference in its entirety). In some embodiments, the wild-type UB comprises the amino acid sequence of SEQ ID NO:1-3, shown at https://world wide web, at the NCBI website, National Library of Medicine at nih.gov/protein/NP_066289.3 (a product of the UBC gene, encoding multimer precursor of ubiquitin; SEQ ID NO: 1). Uniprot entry L8B196 (Uniprot entry about UBC, showing the multimer structure; SEQ ID NO: 2); and Uniprot blast, (/?about=L8B196[1-76]&key=Domain, a BLAST sequence of mature 76 amino acid ubiquitin; SEQ ID NO: 3).

Ubiquitin-Activating Enzymes (E1)

The ubiquitin-activating enzymes (E1) are known in the art. (See, e.g., Schulman et al., Ubiquitin-like protein activation by E1 enzymes: the apex for downstream signaling pathways. *Nat. Rev. Mol. Cell Biol.* 10, 319-331 (2009), the content of which is incorporated herein by reference in its entirety). In some embodiments, the wild-type E1 comprises the amino acid sequence of Uba1 (E1) SEQ ID NO:4 (see https://www.ncbi.nlm.nih.gov/protein/NP_003325.2).

Ubiquitin-Conjugating Enzymes (E2)

The ubiquitin-conjugating enzymes (E2) are known in the art. (See, e.g., Wenzel, et al., E2s: structurally economical and functional replete. *Biochem.* 1 433, 31-42 (2011), the content of which is incorporated herein by reference in its entirety). In some embodiments the wild-type E2 comprises the amino acid sequence of UbcH7/UBE2L3 (E2) SEQ ID NO:5 (see https://www.ncbi.nlm.nih.gov/protein/NP_003338.1)

In some embodiments, the E2 protein comprises UBE2A, UBE2B, UBE2C, UBE2D1, UBE2D2 (UBCH5B), UBE2D3, UBE2D4, UBE2E1, UBE2E2, UBE2E3, UBE2F, UBE2G1, UBE2G2, UBE2H, UBE2I, UBE2J1, UBE2J2, UBE2K, UBE2L3 (UBCH7), UBE2L6, UBE2M UBE2N, UBE2O, UBE2Q1, UBE2Q2, UBE2R1 (CDC34), UBE2R2, UBE2S, UBE2T, UBE2U, UBE2V1, UBE2V2, UBE2W, UBE2Z, ATG3, BIRC6, and UFC1.

Ubiquitin Ligase Enzymes (E3)

The ubiquitin ligase enzymes (E3) are known in the art. (See, e.g., Deshaies, et al., RING domain E3 ubiquitin ligases. *Annu. Rev. Biochem.* 78, 399-434 (2009); and Jin et al., Dual E1 activation systems for ubiquitin differentially regulate E2 enzyme charging. *Nature.* 447, 1135-1138 (2007); the contents of which are incorporated by reference in their entireties.). Several hundred E3 ligases have been identified in the human genome. (See, e.g., Medvar et al., Comprehensive database of human E3 ubiquitin ligases: application to aquaporin-2 regulation. *Physiol Genomics* 2016; 48(7)502-512, the content of which is incorporated herein by reference in its entirety). E3 ligases are predominantly of types referred to as HECT types, U-box types, RBR types, and/or Ring types and a comprehensive library of E3 ligases exists. (See id. citing to (hpcwebapps dot cit.nih.gov front slash ESBL/Database/E3-ligases/). Ubiquitination plays a pivotal role in several cellular processes and is critical for protein degradation and signaling. In the ubiquitination cascade, E3 ubiquitin ligases are responsible for subs rate recognition. In order to achieve selectivity and specificity on their substrates, HECT E3 enzymes are tightly regulated and exert their function in a spatially and temporally controlled fashion in the cells. At their C-terminus, all HECT E3s present the catalytic HECT domain, composed of a bulkier N-terminal lobe (N-lobe) that contains the E2 binding domain, and a C-terminal lobe (C-lobe) carrying the catalytic cysteine (see e.g., FIG. 1). The two lobes are connected by a flexible hinge region that allows the C-lobe to move around in order to facilitate the Ub transfer from the E2 to the E3.

According to the domain organization present in the N-terminal part of the proteins, the HECT E3s can be subdivided into three main families. The best characterized family is the NEDD4 family, including nine human members: ITCH, SMURF1, SMURF2, WWP1, WWP2, NEDD4 NEDD4-2, HECW1, and HECW2. The NEDD4 members share similar domain structure and include a membrane/lipid-binding C2 domain, two to four WW domains for substrate recognition and a C-terminal HECT domain. The second class, the NERC family, is characterized by one or more regulators of chromatin condensation 1 (RCC)-like domains (RLD), which serve as a guanine nucleotide exchange factor (GEF) for the small GTPase in membrane trafficking processes. This family includes six members (HERC1-6) that can be subdivided into four ‘small’ and two ‘large’ HERCs, where the latter. HERC1 and HERC2, are the largest HECT E3s with about 5000 residues. The remaining 13 HECTs do not share specific domains at the N-terminus and, for this reason, are classified as “other” HECT ligases (E6AP, HACE1, TRIP12, UBR5, UBE3B, URE3C, HECTD1, HECTD2, HECTD4, HECTD3, G2D3, and AREL1). See e.g., Weber et Front. Physiol., 3 Apr. 2019. incorporated herein by reference in its entirety).

HECT-E3s ubiquitinate their specific substrate in a two-step process. First, an HECT-E3 binds to an E2 in complex with activated ubiquitin, leading to the formation of a thioester linkage between the C-terminus of ubiquitin and the catalytic cysteine residue in the HECT domain. This transient complex subsequently transfers ubiquitin to an interacting substrate with the formation of an isopeptide bond.

In some embodiments, the wild-type E3 comprises a HECT E3 ligase, and is, for example, HECT-E3 ligase E6AP (also called, interchangeably UBE3A or E6AP/UBE3A), having the amino acid sequence of SEQ ID NO:6 (see https://world wide web dot ncbi dot nlm dot nih dot gov front slash protein/NP_001341435.1).

Structurally, E6AP possesses a Zn2+-binding N-terminal (amino-terminal Zn-finger of Ube3a Ligase (AZUL)) domain and a catalytic HECT domain of ~350 amino acids at the C terminus. A domain necessary for binding with the human papillomavirus (HPV) E6 oncoprotein is located between the AZUL and HECT domains. The AZUL domain is involved in substrate recruitment and also self-inhibitory regulation.

Substrates

In some embodiments, methods, compounds, and compositions of the present disclosure are provided that inhibit, prevent, or decrease, the level of ubiquitination of one or more substrates, thereby treating, ameliorating, or otherwise lessening disease symptoms, progression, and/or severity. By way of example but not by way of limitation, E6AP substrates involved in cancer are shown below in Table 1 (see e.g., Owais, et al., Ref #2, incorporated herein by reference in its entirety).

TABLE 1

E6AP Substrates in Cancer.

| E6AP Substrate | Associated Disorder | Biological Role |
|---|---|---|
| PML | Burkitt’s Lymphoma, Prostate Cancer | Tumor suppressor, controls numerous proteins in PML-NB, induces cellular senescence |
| p27 | Prostate Cancer | Cyclin-dependent kinase inhibitor, prevents progression from $G_1$ to S phase |
| E2F1 | NSCLC | Transcription factor, transactivates cell cycle genes including CDC6, whose product represses the INK4/ARF locus |
| ER-α, PR | Breast Cancer | Steroid receptors/transcription factors, drive expression of proliferative genes |
| ENO 1 | Breast Cancer | Metabolic enzyme, controls energy metabolism and extracellular matrix degradation |
| AIBI | Breast Cancer | Oncoprotein, transcriptional co-activator of ER. |
| p53 | HPV related cancers | Tumor suppressor, induces growth arrest and apoptosis |
| Clusterin | Prostate Cancer | Stress induced chaperone protein, tumor suppressor |
| HHR23A/RAD23A | Breast, Lung Cancer | Nucleotide excision repair protein |

Compounds

Disclosed herein are methods and processes for drug screening and drug discovery. Also disclosed herein are compounds identified in the drug screening methods that are useful for variety of medical and therapeutic applications. In some embodiments, the compounds are formulated into therapeutic compositions and are administered to subjects in need thereof. In some embodiments, the compound of Formula I, isomers, derivatives, or pharmaceutically salts thereof, is provided to a subject in need thereof. Formula I is shown below:

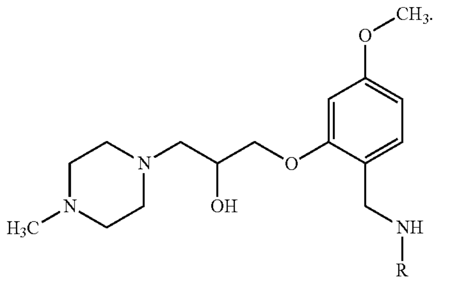

In some embodiments, R is selected from hydrogen, alkyl, cycloalkyl, heterocycloalkyl, aryl optionally substituted with alkyl, and heteroaryl.

In some embodiments, R is selected from:

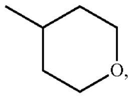

and

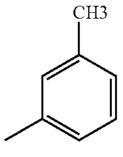

In some embodiments, the compound is one or more of Formula II or III, isomers, derivatives, or pharmaceutically acceptable salts thereof.

Formula II

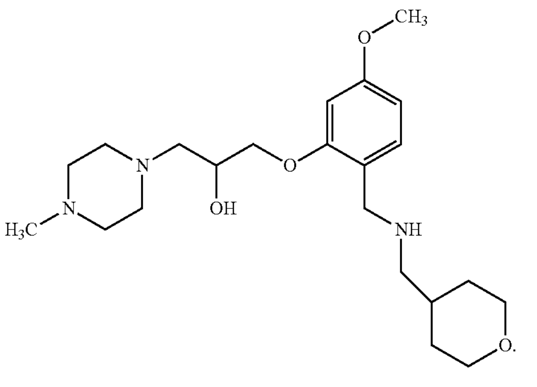

Formula II is the Zinc 23375107 compound, 1-(5-methoxy-2-{[(tetrahydro-2H-pyran-4-ylmethyl)amino]methyl}phenoxy)-3-(4-methyl-1-piperazinyl)-2-propanol, and is shown as compound #3 in FIG. 3.

Formula III

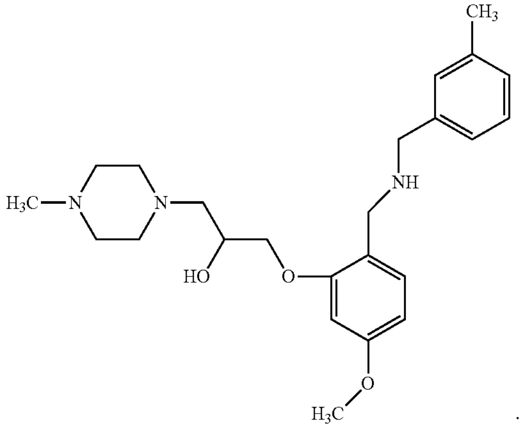

Formula III is #3-1 compound (1-(5-methoxy-2-{[(3-methylbenzyl)amino]methyl}phenoxy)-3-(4-methyl-1-piperazinyl)-2-propanol) and is shown as compound #3-1 in FIG. 4.

Formulations and Modes of Administration

While the compositions disclosed herein may include pharmaceutical compositions comprising any of the compounds disclosed herein (e.g., Formula I, Formula II, Formula III, derivatives, isomers and pharmaceutically acceptable salts thereof), Formula I, derivatives, isomers and pharmaceutically acceptable salts thereof, will be used as an example throughout the discussion of the various embodiments. It is to be understood that any of the compounds disclosed herein can be formulated and administered as described in this section at a dosage effective to treat a subject in need thereof.

Such compositions can be formulated and/or administered in dosages and by techniques well known to those skilled in the medical arts taking into consideration such factors as the age, sex, weight, and condition of the particular patient, and the route of administration.

The compositions may include pharmaceutical solutions comprising carriers, diluents, excipients, and surfactants, as known in the art. Further, the compositions may include preservatives (e.g., anti-microbial or anti-bacterial agents such as benzalkonium chloride). The compositions also may include buffering agents (e.g., in order to maintain the pH of the composition between 6.5 and 7.5).

The pharmaceutical compositions may be administered therapeutically. In therapeutic applications, the compositions are administered to a patient in an amount sufficient to elicit a therapeutic effect (e.g., a response which cures or at least partially arrests or slows symptoms and/or complications of disease (i.e., a "therapeutically effective dose").

In some embodiments, compositions are formulated for systemic delivery, such as oral or parenteral delivery. In some embodiments, minimally invasive microneedles and/or iontophoresis may be used to administer the composition. In some embodiments, compositions are formulated for site-specific administration, such as by injection into a specific tissue or organ, or by topical administration (e.g., by patch applied to the target tissue or target organ, e.g., cancer tissue or brain/neuronal tissue, etc.).

The therapeutic composition may include, in addition to a compound of Formula I, one or more additional active agents. By way of example, the one or more active agents may include an antibiotic, anti-inflammatory agent, a steroid, or a non-steroidal anti-inflammatory drug, and chemotherapeutics.

According to various aspects, a compound of the present disclosure, and optionally the one or more active or inactive agents may be present in the composition as particles or may be soluble. By way of example, in some embodiments, micro particles or microspheres may be employed, and/or nanoparticles may also be employed, e.g., by utilizing biodegradable polymers and lipids to form liposomes, dendrimers, micelles, or nanowafers as carriers for targeted delivery of the compounds. In some embodiments, polymeric implants may be used. By way of example but not by way of limitation, in some embodiments, a therapeutic composition comprising any of the compounds disclosed herein is applied to a patch and placed in contact with the target tissue (e.g., a tumor).

In some embodiments, the composition formulated for administration comprises between 500 mg/ml and 1000 mg/ml of the compound, e.g., a compound comprising Formula I. In some embodiments, the composition formulated for administration comprises between 0.1 ng and 500 mg/ml of the compound, e.g., a compound comprising Formula I. In some embodiments, the compositions if formulated such that between 0.1 ng and 500 μg/ml of the compound (e.g., a compound comprising Formula I) is administered to a subject.

In some embodiments, the methods include administration of the therapeutic compositions once per day; in some embodiments, the composition may be administered multiple times per day, e.g., at a frequency of one or two times per day, or at a frequency of three or four times per day or more. In some embodiments, the methods include administration of the composition once per week, once per month, or as symptoms dictate.

In some embodiments, the composition is administered at between 500 mg/ml and 1000 mg/ml of HECT E3 ligase inhibitor; between 0.1 ng and 500 mg/ml of the inhibitor; or between about 0.1 ng and 500 μg/ml of the inhibitor.

In some embodiments, the treatment reduces, alleviates, prevents, or otherwise lessens the symptoms of the disease or condition more quickly than if no treatment is provided to a subject suffering the same or similar disease, condition, or injury. By way of example, for a subject suffering from cancer, a treated subject would exhibit one or more of reduced tumor size, reduced tumor growth, reduced metastatic activity, reduced swelling near the tumor, and reduced pain, sooner or at a greater degree than a non-treated subject with the same or similar cancer. By way of example, for a subject suffering from a neurological disease or condition, a treated subject would exhibit an improvement in, or a reduced worsening of one or more of the following: sensory response, memory, judgement, speech, writing, general confusion, understanding verbal and/or written communication, eye contact, social interaction, motor coordination and epileptic seizures sooner or at a greater degree than a non-treated subject with the same or similar disease or condition.

In some embodiments, improvements in the condition of the subject's condition is observed more quickly than if no treatment is provided for the same or similar condition or disease.

By way of example, in some embodiments, improvements in the condition is observed within about 1 to about 3 days; within about 3 to about 5 days, or within about a week of the first administration. In some embodiments, improvements in the subject's condition is observed within about 10 days, about 14 days or within about 1 month of the first administration. In some embodiments, improvements in the subject's condition is observed within about 1-3 month, about 3-6 months or within about 1 year of the first administration.

Disease and Conditions

Disclosed herein are compositions useful to treat a subject suffering from, or suspected of having a disease or condition characterized by an increased HECT E3 ligase activity, and/or ectopic HECT E3 ligase activity e.g., UBE3A/E6AP ligase activity.

UBE3A plays important roles not only in brain development but also in viral and non-viral carcinogenesis. Duplication or triplication of 15q11-13 (Dup15q syndrome) renders individuals highly susceptible to autism spectrum disorders (ASD). Indeed, Dup15q is one of the most common cytogenetic anomalies in ASD cohorts. Studies using mouse models of Dup15q suggest that overexpression of UBE3A in neurons accounts for most of the ASD phenotype. It is thought that neurons in developing brain requires proper control of the ubiquitin ligase activity of UBE3A, and excess UBE3A activity could perturb synaptic networks leading to autistic traits.

Excess or ectopic activity of UBE3A could also drive cancer development. The E6 oncoprotein encoded by human papillomavirus (HPV) binds and facilitates UBE3A to ubiquitinate tumor suppressor proteins such as p53 and p27, thus leading to the development of cervical cancer and head/neck cancer.

By way of example only, and not by way of limitation, diseases and conditions include cancer or a neurological disorder (see e.g., Owais et al., Ref. #2, incorporated herein by reference in its entirety). In some embodiments, the cancer is one or more of HPV associated cancer such as cervical, skin and head/neck cancers; HCV associated cancer; cancer characterized by PML downregulation, non-small cell lung cancer, and breast cancer. In some embodiments, the cancer characterized by PML downregulation is one or more of Burkitt's lymphoma and prostate cancer. In some embodiments, the neurological disorder is one or more of Angelman syndrome (AS), Autism Spectrum Disorders (ASD), and chromosome 15q11.2-q13.3 duplication syndrome (Dup15q).

Applications and Advantages

Compounds and compositions disclosed herein (HECT E3 inhibitors) are useful for a number of applications, and exhibit several advantages over known HECT E3 inhibitors. Non-limiting examples include the following.

Use the UBE3A inhibitors as drugs to treat ASD patients, especially those with cytogenic parameters exhibiting Dup15q.

Use the UBE3A inhibitors as drugs to treat patients with HPV-induced cervical, skin and head/neck cancers.

Use the UBE3A inhibitors as drugs to treat patients with non-viral cancers, such as castration-resistant prostate cancers, some of which have been shown to depend on UBE3A activity for their malignant phenotypes.

Use the UBE3A inhibitors as a research reagent to examine the biological functions of UBE3A in various experimental models.

Advantages

A previous report described macrocyclic N-methyl-peptides that bound to the HECT domain of UBE3A and inhibited UBE3A-mediated ubiquitination of p53 (20; PMID: 22195558). However, peptides are generally much more difficult to translate into clinical applications, mostly because of issues in drug delivery to neurons and tumors.

Flavanoid compounds, Luteolin and CAF024, which mimic leucines in the conserved alpha helical motif of UBE3A have been found to inhibit the E6-UBE3A interaction (21, 22; PMID: 24376816, 30875378). Some zinc-ejecting compounds also have been shown to inhibit the E6 interaction with UBE3A (23; PMID: 10413422). However, these approaches are focused on the E6-UBE3A interaction, and will not inhibit the E3 activity of UBE3A in the absence of viral oncoproteins, which is important for treating ASD and non-viral cancers.

N-acetyl phenylalanine has been shown to block UBE3A oligomerization by substituting Phe727 and inhibits its E3 activity at a very high concentration (Ki=12 mM) (24; PMID: 24273172). This is a different way to inhibit the E3, but the efficacy is too low.

Risperidone, a blocker of several neurotransmitter receptors such as dopamine type 2, serotonin type 2, and alpha-adrenergic receptors, is most widely used to treat children with ASD. Risperidone is somewhat effective to improve explosive and aggressive behaviors. However, not all patients with ASD respond to risperidone, and the drug has significant side effects such as weight gain, drowsiness, hormonal changes and involuntary movements. Aripiprazole, which is a serotonin 5-HT2A receptor antagonist and partial agonist of dopamine D2 receptor, is the only other drug approved by FDA to treat irritability of autistic children, but has similar side effects. Thus, there are only limited choices for treatment of ASD, which presents a major unmet need especially for drugs that directly target pathogenic proteins in brain.

To prevent HPV-induced cancers, HPV vaccines have been demonstrated to be quite effective. However, a large number of HPV-infected individuals are still supposed to develop cancers in the coming 10-20 years, and additional targeted therapies to treat those individuals that are already infected is needed. This need is met by the disclosed compounds and compositions.

The compounds and compositions disclosed herein form the first generation of direct small molecule inhibitors of UBE3A. Given the extremely large cohort of ASD patients (1 in 59 US children), economic and impact of development of a new drug for ASD would be extremely high. Even on the assumption that the targeted population for a UBE3A inhibitor is restricted to Dup15q syndrome, its prevalence may be as high as 1 in 5,000 (25; PMID: 23992924). Dup15q is one of the most common cytogenetic alterations in ASD cohorts, and has been found at frequencies of 1:253-1:522 (26, 27, 28; PMID: 19278672, 22424231, 23044707). In addition, 44,000 HPV-associated cancers occur in the United States each year, according to the CDC statistics based on data from 2012-16. Accordingly, the methods, compounds, and compositions of the present disclosure fulfill an unmet need.

To our knowledge, no other small molecule inhibitor against UBE3A has been reported.

EXAMPLES

The following Examples are illustrative and are not intended to limit the scope of the claimed subject matter.

Example 1. In Silico Assessment of UBE3A Structure for Druggable Hotspots

Figure 2A:
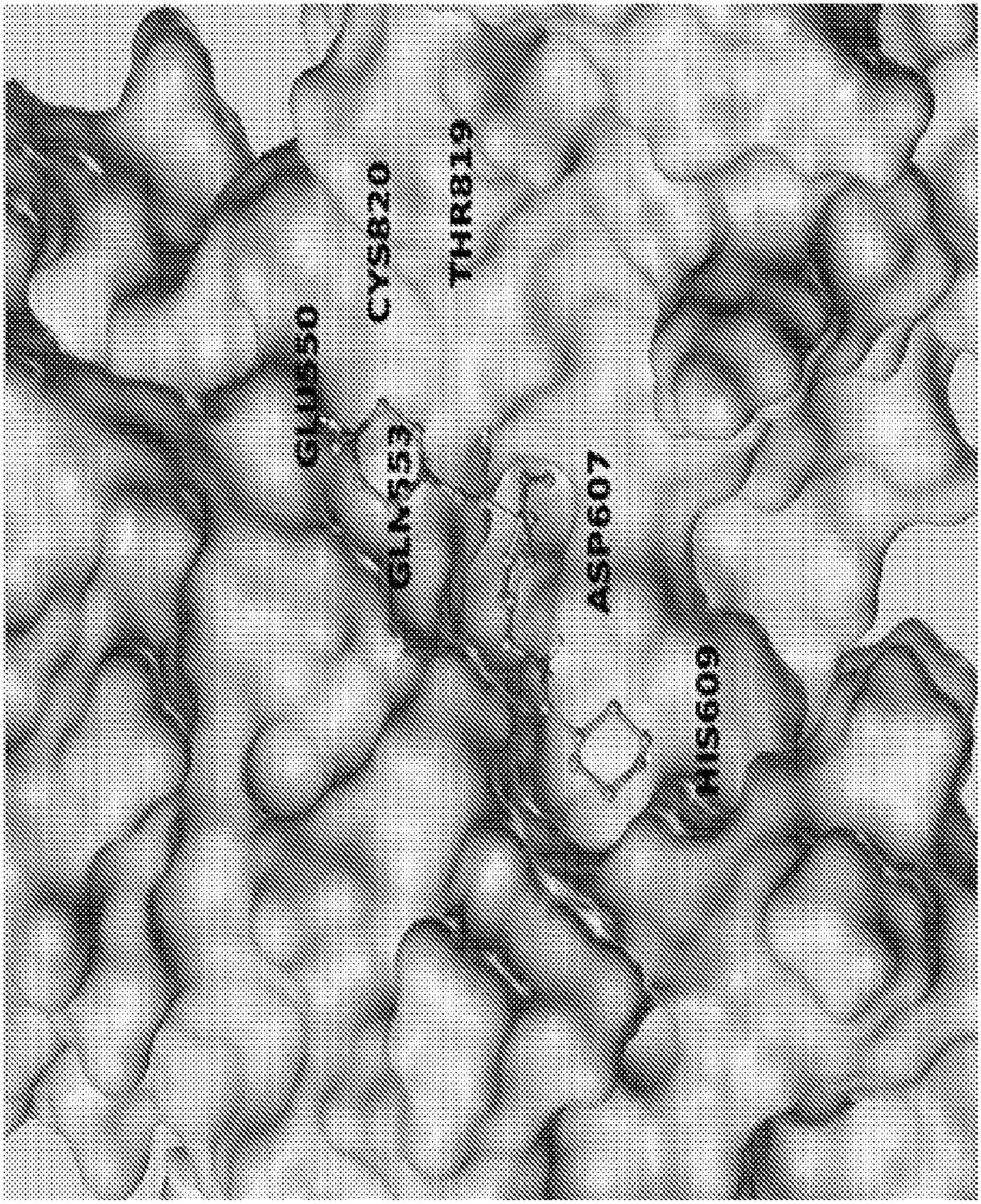
FIG. 2A-B. Structure of the small molecule binding groove in the catalytic domain of UBE3A and its interaction with the Zinc 23375107 compound.
Figure 2B:
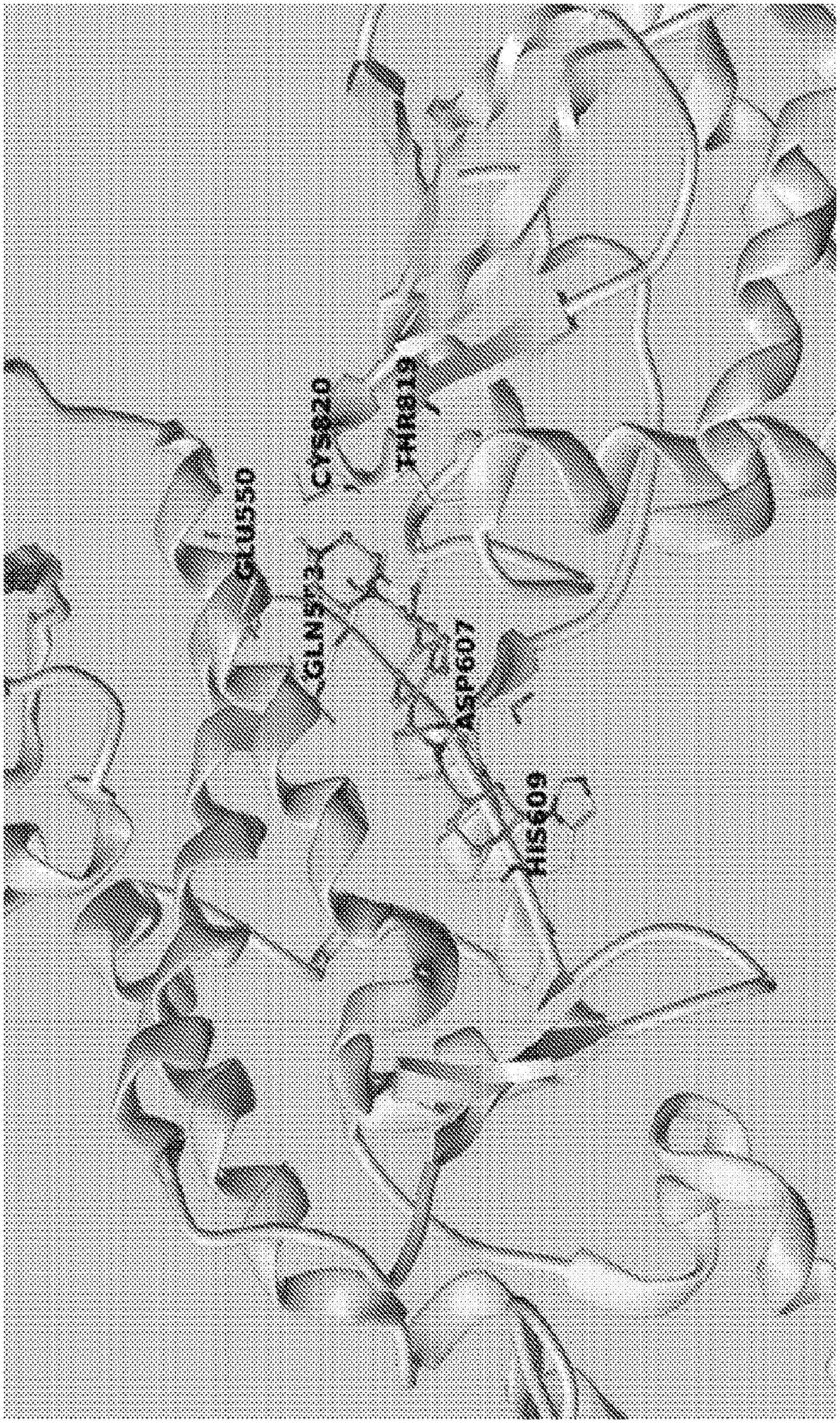

To identify small molecules that bind to the catalytic HECT domain of UBE3A, we analyzed the 3-dimensional (3-D) structure of UBE3A at residues 518-875, which includes the catalytic center C820 residue, according to the X-ray crystal structures published at the database (PDB ID: 1C4Z)(1,2)(FIG. 1). The druggability estimation of a ligand binding pocket has been based on the knowledge obtained from binding pockets for known drugs (3,4). The SiteMap program implemented in the Schrodinger suite (5) correctly identifies 86% of the known binding sites, and it also identifies >98% of binding sites that bind sub-nanomolar ligands (6). Since the implementation of the SiteMap, many modifications have improved the predictive power of the method particularly for flexible and cryptic binding site identification (6). The SiteMap provides a quantitative score (D score) and graphical information which promote assessment of in silico hits, hit-to-lead chemistry and lead optimization of a compound. To enhance the predictive power of the score, Loving et al. (6) introduced Dscore+, which was validated with $^{19}F$ NMR data (7). To analyze the druggability of the HECT domain of UBE3A, we evaluated the Dscore+ as well as the volume of this flexible cryptic pocket and confirmed the druggability criteria (6). We then generated the Connolly surface areas of the two interacting proteins. Close examination of the interfaces of the two interacting partners revealed a putative small molecule binding groove (FIG. 2). It was noted that the I804 residue, which is included in the region, is known to be susceptible for loss-of-function mutations in Angelman syndrome.

Example 2. Virtual High Throughput Screening for Small Molecule that Bind to Hotspots in the UBE3A HECT Domain One of the key elements in any screening campaign is to ensure identified compounds are drug-like and chemically tractable. Often, hits identified through wet HTS campaigns possess non-drug like properties and are unsuitable for chemical modification. We created a curated small molecule database by multiple tiers of filters to the ZINC database (8), which contains approximately 45 million purchasable compounds. We used Lipinski (9), Veber (10) and 239 PAINs filters (11). This proprietary database has been used in all of our successful in silico screening campaigns (12-15). To identify potential UBE3A inhibitors, we screened this library at complexity of 1 million diverse compounds, using the three-tiered Glide (16) small molecule docking engine from Schrodinger. Small molecule hit sets obtained through Glide were cross-docked with Gold (17) and Surflex (18) docking engines, which are built upon orthogonal algorithms, and chose 46 compounds among the top hits (Glide XP Score <−6) for further validation. These hits showed good interactions with the catalytic C820 residue and the Ile-804 (I804) residue critical for the catalytic activity.

Example 3. Validation of Hits by an In Vitro Ubiquitination Assay

We purchased 35 compounds among the 46 hits identified by the initial virtual screen, and tested their abilities to modulate the ubiquitin ligase activity of UBE3A. The in vitro ubiquitination assay was developed using purified ubiquitin (Ub), Uba1 (E1), UbcH7/UBE2L3 (E2), UBE3A (E3), and S5A/Angiocidin/PSMD4 (substrate), as a modification of our previously reported assay (19). The purchased compounds were dissolved in DMSO to generate a stock solution at 10 mM, and then their effects on UBE3A activity were tested by adding each compound at a final concentration of 100 μM. E1, E2 and E3 enzymes were first pre-incubated at 37° C. for 30 min in a buffer containing MgCl2, ATP and each compound. Subsequently, ubiquitin and S5A were added to the reaction and incubated for 60 more minutes. Samples were then analyzed by SDS-PAGE and immunoblotting, and polyubiquitination of the substrate S5A was determined as specific appearance of forms of anti-S5A immunoreactivity at higher molecular weights. FIG. 3 represents the assay, demonstrating that one of the tested compounds (Zinc 23375107, labeled as #3 in FIG. 3) significantly inhibits polyubiquitination of S5A .

The Zinc 23375107 compound, 1-(5-methoxy-2-{[(tetrahydro-2H-pyran-4-ylmethyl)amino]methyl}phenoxy)-3-(4-methyl-1-piperazinyl)-2-propanol, can bind to the cleft near the catalytic center (Cys-820, C820) and one of the residues critical for the activity (Glu-550, E550) (FIG. 2).

We then examined effects of varying concentrations of Zinc 23375107, named as compound #3, on polyubiquitination of S5A (FIG. 5A). This compound exhibited dosage-dependent inhibition of S5A polyubiquitination. We estimated the IC50 of the compound around 100 μM. While this compound consistently inhibits the ubiquitin ligase activity of UBE3A, its potency was weak, suggesting the necessity of identifying more potent compounds structurally analogous to it.

Example 4. Search for UBE3A Inhibitors with Better Efficacy

To identify more potent UBE3A inhibitor compounds than Zinc 23375107, we conducted in silico search for compounds that are structurally analogous to Zinc 23375107 (with similarity varying from 0.99-0.80) and could bind to the druggable hotspot of UBE3A. This second screen identified 140 compounds, of which 8 have been tested by the in vitro ubiquitination assay. We found that one of the eight compounds was capable of inhibiting the UBE3A-mediated polyubiquitination of S5A substrate at 100 μM (FIG. 4), and named it as compound #3-1, which is 1-(5-methoxy-2-{[(3-methylbenzyl)amino]methyl}phenoxy)-3-(4-methyl-1-piperazinyl)-2-propanol (see FIG. 4B). Our experiments using titrating amounts of #3-1 suggested that this compound is a modestly more potent UBE3A inhibitor than the parental #3 compound, and preliminary data showed that the IC50 of this compound is still relatively high in the range of 10 μM (FIG. 5B). This observation indicates that we need to look for more potent inhibitors that are structurally analogous to compounds #3 and #3-1. Therefore, we added more purchasable drug-like compounds to the library and repeated the screen for compounds analogous to #3 with potential binding to the druggable hotspot of UBE3A. This latest screen provided a list of 30 potential inhibitors, and we are currently testing them by the in vitro ubiquitination assay.

Example 5. Fluorescence Thermal Shift Assay to Demonstrate Physical Interaction Between the Compound #3.1 and the HECT Domain of UBE3A To verify the physical interaction between the HECT domain of UBE3A and the identified compounds and also develop a high throughput assay for further screening, we have developed a fluorescence thermal shift analysis (FTS). we have prepared a truncated UBE3A protein (residues 495-852 of isoform 1) using *E. coli* and performed preliminary FTS test (FIG. 6). The recombinant HECT domain of UBE3A showed a well-defined melting profile. Moreover, the melting profile was significantly modulated by compound #3-1. The FTS method has been widely used for measurement of protein-ligand interaction (Reference https://world wide web, at ncbi dot nlm dot nih dot gov front slash pubmed front slash 24590724). FTS monitors protein thermal denaturation using Sypro-Orange which fluoresces when bound to hydrophobic surfaces, taking advantage of the changes in hydrophobic surface exposure in protein denaturation. Small molecule binding affects protein thermal stability, therefore can be detected through a shift in protein's thermal denaturation (melting) temperature (Tm). These data suggest that the compound #3-1 physically binds to the HECT domain of UBE3A and inhibits its E3 activity, as hypothesized.

Example 6. Cytotoxicity of the Compound #3.1 in HPV-Positive Cancer Cells

Figure 7:
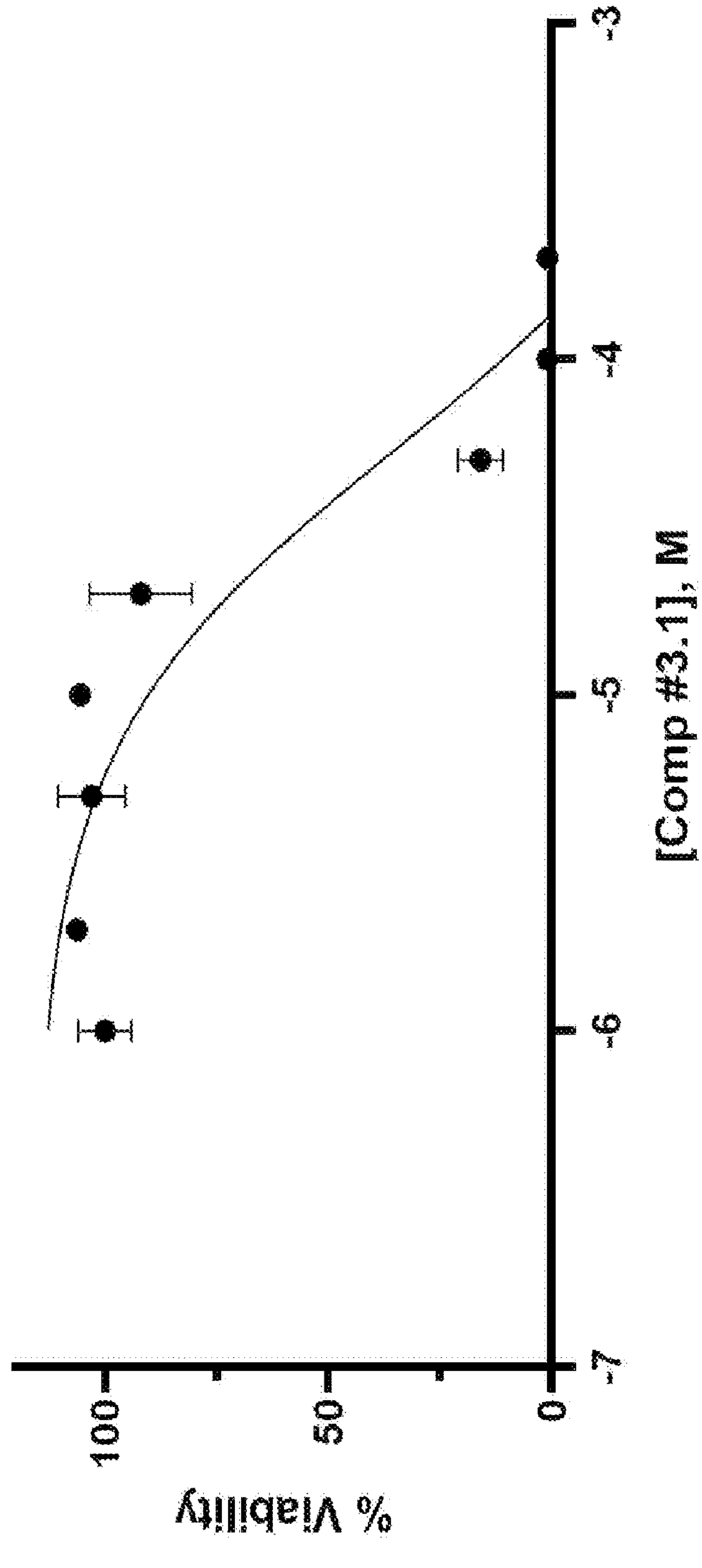
FIG. 7. Cytotoxicity of the hit compound #3-1 in HPV-positive cervical cancer cells. HPV18-positive human cervical cancer HeLa cells were incubated for 72 hrs with the compound #3-1 at the indicated concentrations, followed by determination of cell viability by the alamarBlue™ HS Cell Viability Reagent (Thermo). Data are shown as means±SEM, and the EC50 is estimated to be 30 μM.

We have recently tested whether the compound #3.1 exert any cytotoxic action in HPV-positive cancer cells. Human cervical carcinoma HeLa cells are a widely used HPV18-positive cell lines. We incubated HeLa cells with the compound #3.1 at various concentrations for 72 hours and determined viability of the cells (FIG. 7). This study has shown that the compound #3.1 exerts cytotoxicity in a dose-dependent manner with EC50 at 30 μM. The data suggest that small molecule-based inhibition of UBE3A leads to cell death in the presence of HPV oncoproteins, and more potent UBE3A inhibitors may be used as a therapeutic agent against human HPV-positive cancers.

REFERENCES

1. Huang, L., Kinnucan, E., Wang, G., Beaudenon, S., Howley, P. M., Huibregtse, J. M., and Pavletich, N. P. (1999) Structure of an E6AP-UbcH7 complex: insights into ubiquitination by the E2-E3 enzyme cascade. *Science* 286, 1321-1326, https://www.ncbi.nlm.nih.gov/pubmed/10558980
2. Owais, A., Mishra, R. K., and Kiyokawa, H. (2020) The HECT E3 Ligase E6AP/UBE3A as a Therapeutic Target in Cancer and Neurological Disorders. *Cancers* (*Basel*) 12, 2108, https://www.ncbi.nlm.nih.gov/pubmed/32751183
3. Hopkins, A. L., and Groom, C. R. (2002) The druggable genome. *Nat Rev Drug Discov* 1, 727-730, https://www.ncbi.nlm.nih.gov/pubmed/112209152.
4. Cheng, A. C., Coleman, R. G., Smyth, K. T., Cao, Q., Soulard, P., Caffrey, D. R., Salzberg, A. C., and Huang, E. S. (2007) Structure-based maximal affinity model predicts small-molecule druggability. *Nat Biotechnol* 25, 71-75, https://www.ncbi.nlm.nih.gov/pubmed/17211405
5. Halgren, T. A. (2009) Identifying and characterizing binding sites and assessing druggability. *J Chem Inf Model* 49, 377-389, https://www.ncbi.nlm.nih.gov/pubmed/19434839
6. Loving, K. A., Lin, A., and Cheng, A. C. (2014) Structure-based druggability assessment of the mammalian structural proteome with inclusion of light protein flexibility. *PLoS Comput Biol* 10, e1003741, [4117425], https://www.ncbi.nlm.nih.gov/pubmed/25079060
7. Jordan, J. B., Poppe, L., Xia, X., Cheng, A. C., Sun, Y., Michelsen, K., Eastwood, H., Schnier, P. D., Nixey, T., and Zhong, W. (2012) Fragment based drug discovery: practical implementation based on (1)(9)F NMR spectroscopy. *J Med Chem* 55, 678-687, https://www.ncbi.nlm.nih.gov/pubmed/22165820
8. Sterling, T., and Irwin, J. J. (2015) ZINC 15—Ligand Discovery for Everyone. *J Chem Inf Model* 55, 2324-2337, [PMC4658288], https://www.ncbi.nlm.nih.gov/pubmed/26479676

9. Lipinski, C. A. (2004) Lead- and drug-like compounds: the rule-of-five revolution. *Drug Discov Today Technol* 1, 337-341, https://www.ncbi.nlm.nih.gov/pubmed/24981612

10. Wan-Mamat, W. M., Isa, N. A., Wahab, H. A., and Wan-Mamat, W. M. (2009) Drug-like and non drug-like pattern classification based on simple topology descriptor using hybrid neural network. *Conf Proc IEEE Eng Med Biol Soc* 2009, 6424-6427, https://www.ncbi.nlm.nih.gov/pubmed/19964424

11. Baell, J. B., and Holloway, G. A. (2010) New substructure filters for removal of pan assay interference compounds (PAINS) from screening libraries and for their exclusion in bioassays. *J Med Chem* 53, 2719-2740, https://www.ncbi.nlm.nih.gov/pubmed/20131845

12. Mishra, R. K., and Singh, J. (2015) A Structure Guided QSAR: A Rapid and Accurate technique to predict IC50: A Case Study. *Curr Comput Aided Drug Des* 11, 152-163, https://www.ncbi.nlm.nih.gov/pubmed/26135341

13. Mishra, R. K., Shum, A. K., Platanias, L. C., Miller, R. J., and Schiltz, G. E. (2016) Discovery and characterization of novel small-molecule CXCR4 receptor agonists and antagonists. *Sci Rep* 6, 30155, [PMC4960487], https://www.ncbi.nlm.nih.gov/pubmed/27456816

14. Klionsky, D. J., Abdelmohsen, K., Abe, A., Abedin, M. J., Abeliovich, H., Acevedo Arozena, A., Adachi, H., Adams, C. M., Adams, P. D., Adeli, K., Adhihetty, P. J., Adler, S. G., Agam, G., Agarwal, R., Aghi, M. K., et al. (2016) Guidelines for the use and interpretation of assays for monitoring autophagy (3rd edition). *Autophagy* 12, 1-222, [PMC4835977], https://www.ncbi.nlm.nih.gov/pubmed/26799652

15. Villa, S. R., Mishra, R. K., Zapater, J. L., Priyadarshini, M., Gilchrist, A., Mancebo, H., Schiltz, G. E., and Layden, B. T. (2017) Homology modeling of FFA2 identifies novel agonists that potentiate insulin secretion. *J Investig Med* 65, 1116-1124, https://www.ncbi.nlm.nih.gov/pubmed/28784695

16. Sherman, W., Day, T., Jacobson, M. P., Friesner, R. A., and Farid, R. (2006) Novel procedure for modeling ligand/receptor induced fit effects. *J Med Chem* 49, 534-553, https://www.ncbi.nlm.nih.gov/pubmed/16420040

17. Verdonk, M. L., Chessari, G., Cole, J. C., Hartshorn, M. J., Murray, C. W., Nissink, J. W., Taylor, R. D., and Taylor, R. (2005) Modeling water molecules in protein-ligand docking using GOLD. *J Med Chem* 48, 6504-6515, https://www.ncbi.nlm.nih.gov/pubmed/16190776

18. Jain, A. N. (2003) Surflex: fully automatic flexible molecular docking using a molecular similarity-based search engine. *J Med Chem* 46, 499-511, https://www.ncbi.nlm.nih.gov/pubmed/12570372

19. Wang, Y., Liu, X., Duong, D. M., Bhuripanyo, K., Zhao, B., Bi, Y., Kiyokawa, H., and Yin, J. (2017) Identifying the ubiquitination targets of E6AP by Orthogonal Uniquitin Transfer. *Nature Communications* 8, 2232, https://www.ncbi.nlm.nih.gov/pubmed/29263404

20. Yamagishi, et al., Chem Biol. 2011 Dec. 23; 18(12): 1562-70 (PMID:22195558).

21. Cherry et al., PLoS One. 2013 Dec. 23; 8(12):e84506. doi: 10.1371/journal.pone.0084506. eCollection 2013 (PMID: 24376816).

22. Ricci-Lopez et al., PLoS One 2019 Mar. 15; 14(3): e0213028. doi: 10.1371/journal.pone.0213028.eCollection 2019 (PMID: 30875378).

23. Beerheide, et al., J Natl Cancer Inst. 1999 Jul. 21; 91(14):1211-20. doi: 10.1093/jnci/91.14.1211 (PMID: 10413422).

24. Ronchi, et al., J Biol Chem 2014 Jan. 10; 289(2): 1033-48. doi: 10.1074/jbc.M113.517805. Epub 2013 Nov. 22 (PMID: 24273172).

25. Kirov, et al., Biol Psychiatry 2014 Mar. 1; 75(5):378-85. doi: 10.1016/j.biopsych.2013.07.022. Epub 2013 Aug. 28 (PMID: 23992924).

26. Depienne et al., Biol Psychiatry. 2009 Aug. 15; 66(4):349-59. doi: 10.1016/j.biopsych.2009.01.025. Epub 2009 Mar. 17 (PMID: 19278672).

27. Malhortra, et al., Cell 2012 Mar. 16; 148(6):1223-41. doi: 10.1016/j.cell.2012.02.039. (PMID: 22424231).

28. De-luca et al., Mol Psychiatry 2013 October; 18(10): 1090-5. doi: 10.1038/mp.2012.138. Epub 2012 Oct. 9 (PMID:23044707).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

SEQUENCES

This is a product of UBC gene, encoding multimer precursor of ubiquitin
LOCUS NP_066289 685 aa linear PRI 12 Dec. 2020
DEFINITION polyubiquitin-C [*Homo sapiens*].
ACCESSION NP_066289 XP_947802 XP_951381-XP_951420
VERSION NP_066289.3

SEQ ID NO: 1

```
  1   mqifvktltg ktitleveps dtienvkaki qdkegippdq qrlifagkql edgrtlsdyn
 61   iqkestlhlv lrlrggmqif vktltgktit levepsdtie nvkakiqdke gippdqqrli
121   fagkqledgr tlsdyniqke stlhlvlrlr ggmqifvktl tgktitleve psdtienvka
181   kiqdkegipp dqqrlifagk qledgrtlsd yniqkestlh lvlrlrggmq ifvktltgkt
241   itlevepsdt ienvkakiqd kegippdqqr lifagkqled grtlsdyniq kestlhlvlr
301   lrggmqifvk tltgktitle vepsdtienv kakiqdkegi ppdqqrlifa gkqledgrtl
361   sdyniqkest lhlvlrlrgg mqifvktltg ktitleveps dtienvkaki qdkegippdq
421   qrlifagkql edgrtlsdyn iqkestlhlv lrlrggmqif vktltgktit levepsdtie
481   nvkakiqdke gippdqqrli fagkqledgr tlsdyniqke stlhlvlrlr ggmqifvktl
541   tgktitleve psdtienvka kiqdkegipp dqqrlifagk qledgrtlsd yniqkestlh
601   lvlrlrggmq ifvktltgkt itlevepsdt ienvkakiqd kegippdqqr lifagkqled
661   grtlsdyniq kestlhlvlr lrggv
```

UniProtKB-L8B196 (L8B196_HUMAN)
This is a Uniprot entry about UBC, showing the multimer structure.

SEQ ID NO: 2

```
        10         20         30         40         50
MQIFVKTLTG KTITLEVEPS DTIENVKAKI QDKEGIPPDQ QRLIFAGKQL

        60         70         80         90        100
EDGRTLSDYN IQKESTLHLV IRLRGGMQIF VKTLTGKTIT LEVEPSDTIE

       110        120        130        140        150
NVKAKIQDKE GIPPDQQRLI FAGKQLEDGR TLSDYNIQKE STLHLVLRLR

       160        170        180        190        200
GGMQIFVKTL TGKTITLEVE PSDTIENVKA KIQDKEGIPP DQQRLIFAGK

       210        220        230        240        250
QLEDGRTLSD YNIQKESTLH LVLRLRGGMQ IFVKTLTGKT ITLEVEPSDT

       260        270        280        290        300
IENVKAKVQD KEGIPPDQQR LIFAGKQLED GRTLSDYNIQ KESTLHLVLR

       310        320        330        340        350
LRGGMQIFVK TLTGKTITLE VEPSDTIENV KAKIQDKEGI PPDQQRLIFA

       360        370        380        390        400
GKQLEDGRTL SDYNIQKEST LHLVERLRGG MQIFVKTLTG KAITLEVEPS

       410        420        430        440        450
DTIENVKAKI QDKEGIPPDQ QRLIFAGKQL EDGRTLSDYN IQKESTLHLV

       460        470        480        490        500
LRLRGGMQIF VKTLTGKTIT LEVEPSDTIE NVKAKIQDKE GIPPDQQRLI

       510        520        530
FAGKQLEDGR TLSDYNIQKE STLHLVLRLR GGV
```

This shows BLAST sequence of mature 76 aa ubiquitin
>tr|L8B196|1-76

SEQ ID NO: 3

```
MQIFVKTLTGKTITLEVEPSDTIENVKAKIQDKEGIPPDQQRLIFAGKQLEDGRTLSDYN

IQKESTLHLVLRLRGG
```

LOCUS NP_003325 1058 aa linear PRI 10 Dec. 2020
DEFINITION ubiquitin-like modifier-activating enzyme 1 [*Homo sapiens*].
ACCESSION NP_003325
VERSION NP_003325.2
DBSOURCE REFSEQ: accession NM_003334.4

-continued

KEYWORDS RefSeq; MANE Select.
SOURCE *Homo sapiens* (human)

SEQ ID NO: 4

```
   1 msssplskkr rvsgpdpkpg sncspaqsvl sevpsvptng makngseadi deglysrqly
  61 vlgheamkrl qtssvlvsgl rglgveiakn iilggvkavt lhdqgtaqwa dlssqfylre
 121 edigknraev sqprlaelns yvpvtaytgp lvedflsgfq vvvltntple dqlrvgefch
 181 nrgiklvvad trglfgqlfc dfgeemiltd sngeqplsam vsmvtkdnpg vvtcldearh
 241 gfesgdfvsf sevqgmveln gnqpmeikvl gpytfsicdt snfsdyirgg ivsqvkvpkk
 301 isfkslvasl aepdfvvtdf akfsrpaqlh igfqalhqfc aqhgrpprpr needaaelva
 361 laqavnaral pavqqnnlde dlirklayva agdlapinaf igglaaqevm kacsgkfmpi
 421 mqwlyfdale clpedkevlt edkclqrqnr ydgqvavfgs dlqeklgkqk yflvgagaig
 481 cellknfami glgcgeggei ivtdmdtiek snlnrqflfr pwdvtklksd taaaavrqmn
 541 phirvtshqn rvgpdteriy dddffqnldg vanaldnvda rmymdrrcvy yrkpllesgt
 601 lgtkgnvqvv ipfltesyss sqdppeksip ictlknfpna iehtlqward efeglfkqpa
 661 envnqyltdp kfvertlrla gtqplevlea vqrslvlqrp qtwadcvtwa chhwhtqysn
 721 nirqllhnfp pdqltssgap fwsgpkrcph pltfdvnnpl hldyvmaaan lfaqtygltg
 781 sqdraavatf lqsvqvpeft pksgvkihvs dqelqsanas vddsrleelk atlpspdklp
 841 gfkmypidfe kdddsnfhmd fivaasnlra enydipsadr hkskliagki ipaiatttaa
 901 vvglvclely kvvqghrqld sykngflnla lpffgfsepl aaprhqyynq ewtlwdrfev
 961 qglqpngeem tlkqfldyfk tehkleitml sqgvsmlysf fmpaaklker ldqpmteivs
1021 rvskrklgrh vralvlelcc ndesgedvev pyvrytir
```

LOCUS NP_003338 154 aa linear PRI 20 Dec. 2020
DEFINITION ubiquitin-conjugating enzyme E2 L3 isoform 1 [*Homo sapiens*].
ACCESSION NP_003338
VERSION NP_003338.1
DBSOURCE REFSEQ: accession NM_003347.4
KEYWORDS RefSeq; MANE Select.
SOURCE *Homo sapiens* (human)

SEQ ID NO: 5

```
   1 maasrrlmke leeirkcgmk nfrniqvdea nlltwqgliv pdnppydkga frieinfpae
  61 ypfkppkitf ktkiyhpnid ekgqvclpvi saenwkpatk tdqviqslia lvndpqpehp
 121 lradlaeeys kdrkkfckna eeftkkygek rpvd
```

LOCUS NP_001341435 852 aa linear PRI 13 Dec. 2020
DEFINITION ubiquitin-protein ligase E3A isoform 1 [*Homo sapiens*].
ACCESSION NP_001341435 XP_005268326
VERSION NP_001341435.1
DBSOURCE REFSEQ: accession NM_001354506.2
KEYWORDS RefSeq.
SOURCE *Homo sapiens* (human)

SEQ ID NO: 6

```
   1 mkraaakhli eryyhqlteg cgneactnef cascptflrm dnnaaaikal elykinaklc
  61 dphpskkgas saylenskga pnnscseikm nkkgaridfk dvtylteekv yeilelcrer
 121 edysplirvi grvfssaeal vqsfrkvkqh tkeelkslqa kdedkdedek ekaacsaaam
 181 eedseasssr igdssqgdnn lqklgpddvs vdidairrvy trllsnekie taflnalvyl
 241 spnvecdlty hnvysrdpny lnlfiivmen rnlhspeyle malplfckam sklplaaqgk
 301 lirlwskyna dqirrmmetf qqlitykvis nefnsrnlvn dddaivaask clkmvyyanv
 361 vggevdtnhn eeddeepipe sseltlqell geerrnkkgp rvdpletelg vktldcrkpl
 421 ipfeefinep lnevlemdkd ytffkveten kfsfmtcpfi lnavtknlgl yydnrirmys
 481 erritvlysl vqgqqlnpyl rlkvrrdhii ddalvrlemi amenpadlkk qlyvefegeq
 541 gvdeggvske ffqlvveeif npdigmftyd estklfwfnp ssfetegqft ligivlglai
```

-continued 601 ynncildvhf pmvvyrklmg kkgtfrdlgd shpvlyqslk dlleyegnve ddmmitfqis 661 qtdlfgnpmm ydlkengdki pitnenrkef vnlysdyiln ksvekqfkaf rrgfhmvtne 721 splkylfrpe eiellicgsr nldfqaleet teydggytrd svlirefwei vhsftdeqkr 781 lflqfttgtd rapvgglgkl kmiiakngpd terlptshtc fnvlllpeys skeklkerll 841 kaityakgfg ml

We claim:

1. A method for inhibiting the activity of a HECT E3 ubiquitin ligase in a subject in need thereof, the method comprising: administering an effective amount of a compound of Formula I, a stereoisomer thereof, a pharmaceutically acceptable salt thereof, or a combination thereof, wherein Formula I is:

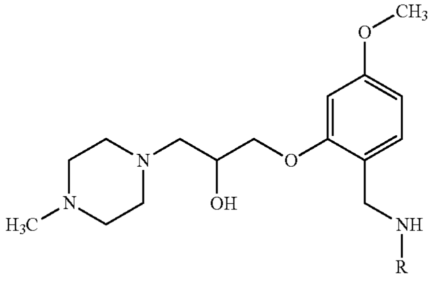

wherein R is selected from hydrogen, alkyl, cycloalkyl, heterocycloalkyl, aryl optionally substituted with alkyl, and heteroaryl.

2. The method of claim 1, wherein R is selected from:

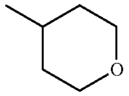

and

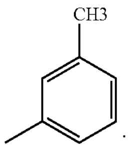

3. The method of claim 1, wherein the compound comprises Formula II:

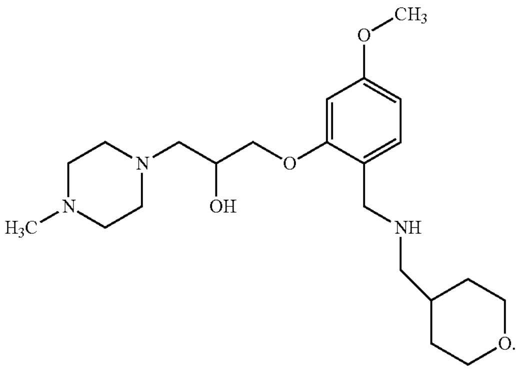 [SMILES: COc1ccc(CNCC2CCOCC2)c(OCC(O)CN2CCN(C)CC2)c1]

4. The method of claim 1, wherein the compound comprises Formula III:

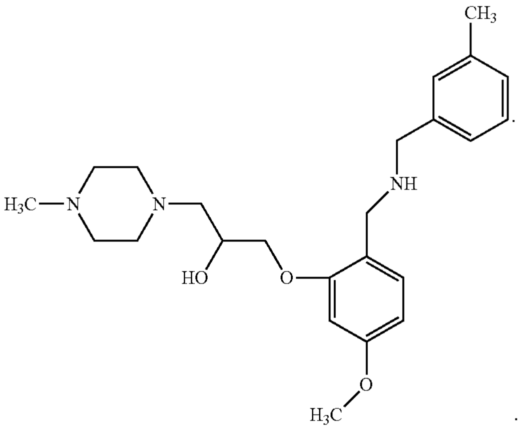 [SMILES: COc1ccc(CNCc2cccc(C)c2)c(OCC(O)CN2CCN(C)CC2)c1]

5. The method of claim 1, wherein the subject in need thereof is diagnosed with or is suspected of having a disease or condition characterized by increased HECT E3 ubiquitin ligase activity.

6. The method of claim 5, wherein the HECT E3 ubiquitin ligase comprises UBE3A/E6AP.

7. The method of claim 6, wherein the disease or condition is cancer or a neurological disorder.

8. The method of claim 7, wherein the cancer is one or more of HPV associated cancer, HCV associated cancer, cancer characterized by PML downregulation, non-small cell lung cancer, and breast cancer.

9. The method of claim 8 wherein the cancer characterized by PML downregulation is one or more of Burkitt's lymphoma and prostate cancer.

10. The method of claim 7, wherein the neurological disorder is one or more of Angelman syndrome (AS), Autism Spectrum Disorder (ASD), and chromosome 15q11.2-q13.3 duplication syndrome (Dup15q).

11. The method of claim 1, wherein the compound is formulated as a pharmaceutical composition.

12. The method of claim 1, wherein the compound is administered to the subject orally, parenterally, topically, or locally.

* * * * *

SEQUENCE LISTING

<160> NUMBER OF SEQ ID NOS: 6

<210> SEQ ID NO 1
<211> LENGTH: 685
<212> TYPE: PRT
<213> ORGANISM: Homo sapiens

<400> SEQUENCE: 1

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ser Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Pro Ser Asp Thr Ile Glu
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ser Asp Tyr Asn Ile Gln Lys Glu Ser Thr Leu His Leu Val Leu Arg
    210                 215                 220

Leu Arg Gly Gly Met Gln Ile Phe Val Lys Thr Leu Thr Gly Lys Thr
225                 230                 235                 240

Ile Thr Leu Glu Val Glu Pro Ser Asp Thr Ile Glu Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ser Asp Tyr Asn
        275                 280                 285

Ile Gln Lys Glu Ser Thr Leu His Leu Val Leu Arg Leu Arg Gly Gly
    290                 295                 300
```

-continued

```
Met Gln Ile Phe Val Lys Thr Leu Thr Gly Lys Thr Ile Thr Leu Glu
305                 310                 315                 320

Val Glu Pro Ser Asp Thr Ile Glu Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ser Asp Tyr Asn Ile Gln Lys Glu
        355                 360                 365

Ser Thr Leu His Leu Val Leu Arg Leu Arg Gly Gly Met Gln Ile Phe
    370                 375                 380

Val Lys Thr Leu Thr Gly Lys Thr Ile Thr Leu Glu Val Glu Pro Ser
385                 390                 395                 400

Asp Thr Ile Glu Asn Val Lys Ala Lys Ile Gln Asp Lys Glu Gly Ile
                405                 410                 415

Pro Pro Asp Gln Gln Arg Leu Ile Phe Ala Gly Lys Gln Leu Glu Asp
            420                 425                 430

Gly Arg Thr Leu Ser Asp Tyr Asn Ile Gln Lys Glu Ser Thr Leu His
        435                 440                 445

Leu Val Leu Arg Leu Arg Gly Gly Met Gln Ile Phe Val Lys Thr Leu
    450                 455                 460

Thr Gly Lys Thr Ile Thr Leu Glu Val Glu Pro Ser Asp Thr Ile Glu
465                 470                 475                 480

Asn Val Lys Ala Lys Ile Gln Asp Lys Glu Gly Ile Pro Pro Asp Gln
                485                 490                 495

Gln Arg Leu Ile Phe Ala Gly Lys Gln Leu Glu Asp Gly Arg Thr Leu
            500                 505                 510

Ser Asp Tyr Asn Ile Gln Lys Glu Ser Thr Leu His Leu Val Leu Arg
        515                 520                 525

Leu Arg Gly Gly Met Gln Ile Phe Val Lys Thr Leu Thr Gly Lys Thr
    530                 535                 540

Ile Thr Leu Glu Val Glu Pro Ser Asp Thr Ile Glu Asn Val Lys Ala
545                 550                 555                 560

Lys Ile Gln Asp Lys Glu Gly Ile Pro Pro Asp Gln Gln Arg Leu Ile
                565                 570                 575

Phe Ala Gly Lys Gln Leu Glu Asp Gly Arg Thr Leu Ser Asp Tyr Asn
            580                 585                 590

Ile Gln Lys Glu Ser Thr Leu His Leu Val Leu Arg Leu Arg Gly Gly
        595                 600                 605

Met Gln Ile Phe Val Lys Thr Leu Thr Gly Lys Thr Ile Thr Leu Glu
    610                 615                 620

Val Glu Pro Ser Asp Thr Ile Glu Asn Val Lys Ala Lys Ile Gln Asp
625                 630                 635                 640

Lys Glu Gly Ile Pro Pro Asp Gln Gln Arg Leu Ile Phe Ala Gly Lys
                645                 650                 655

Gln Leu Glu Asp Gly Arg Thr Leu Ser Asp Tyr Asn Ile Gln Lys Glu
            660                 665                 670

Ser Thr Leu His Leu Val Leu Arg Leu Arg Gly Gly Val
        675                 680                 685
```

<210> SEQ ID NO 2
<211> LENGTH: 533
<212> TYPE: PRT
<213> ORGANISM: Homo sapiens -continued

<400> SEQUENCE: 2

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ser Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Pro Ser Asp Thr Ile Glu
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ser Asp Tyr Asn Ile Gln Lys Glu Ser Thr Leu His Leu Val Leu Arg
    210                 215                 220

Leu Arg Gly Gly Met Gln Ile Phe Val Lys Thr Leu Thr Gly Lys Thr
225                 230                 235                 240

Ile Thr Leu Glu Val Glu Pro Ser Asp Thr Ile Glu Asn Val Lys Ala
                245                 250                 255

Lys Val Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ser Asp Tyr Asn
        275                 280                 285

Ile Gln Lys Glu Ser Thr Leu His Leu Val Leu Arg Leu Arg Gly Gly
    290                 295                 300

Met Gln Ile Phe Val Lys Thr Leu Thr Gly Lys Thr Ile Thr Leu Glu
305                 310                 315                 320

Val Glu Pro Ser Asp Thr Ile Glu Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ser Asp Tyr Asn Ile Gln Lys Glu
        355                 360                 365

Ser Thr Leu His Leu Val Leu Arg Leu Arg Gly Gly Met Gln Ile Phe
    370                 375                 380

Val Lys Thr Leu Thr Gly Lys Ala Ile Thr Leu Glu Val Glu Pro Ser
385                 390                 395                 400

Asp Thr Ile Glu Asn Val Lys Ala Lys Ile Gln Asp Lys Glu Gly Ile
                405                 410                 415
```

```
Pro Pro Asp Gln Gln Arg Leu Ile Phe Ala Gly Lys Gln Leu Glu Asp
            420                 425                 430

Gly Arg Thr Leu Ser Asp Tyr Asn Ile Gln Lys Glu Ser Thr Leu His
        435                 440                 445

Leu Val Leu Arg Leu Arg Gly Gly Met Gln Ile Phe Val Lys Thr Leu
    450                 455                 460

Thr Gly Lys Thr Ile Thr Leu Glu Val Glu Pro Ser Asp Thr Ile Glu
465                 470                 475                 480

Asn Val Lys Ala Lys Ile Gln Asp Lys Glu Gly Ile Pro Pro Asp Gln
                485                 490                 495

Gln Arg Leu Ile Phe Ala Gly Lys Gln Leu Glu Asp Gly Arg Thr Leu
            500                 505                 510

Ser Asp Tyr Asn Ile Gln Lys Glu Ser Thr Leu His Leu Val Leu Arg
        515                 520                 525

Leu Arg Gly Gly Val
    530


<210> SEQ ID NO 3
<211> LENGTH: 76
<212> TYPE: PRT
<213> ORGANISM: Homo sapiens

<400> SEQUENCE: 3

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75


<210> SEQ ID NO 4
<211> LENGTH: 1058
<212> TYPE: PRT
<213> ORGANISM: Homo sapiens

<400> SEQUENCE: 4

Met Ser Ser Ser Pro Leu Ser Lys Lys Arg Arg Val Ser Gly Pro Asp
1               5                   10                  15

Pro Lys Pro Gly Ser Asn Cys Ser Pro Ala Gln Ser Val Leu Ser Glu
            20                  25                  30

Val Pro Ser Val Pro Thr Asn Gly Met Ala Lys Asn Gly Ser Glu Ala
        35                  40                  45

Asp Ile Asp Glu Gly Leu Tyr Ser Arg Gln Leu Tyr Val Leu Gly His
    50                  55                  60

Glu Ala Met Lys Arg Leu Gln Thr Ser Ser Val Leu Val Ser Gly Leu
65                  70                  75                  80

Arg Gly Leu Gly Val Glu Ile Ala Lys Asn Ile Ile Leu Gly Gly Val
                85                  90                  95

Lys Ala Val Thr Leu His Asp Gln Gly Thr Ala Gln Trp Ala Asp Leu
            100                 105                 110

Ser Ser Gln Phe Tyr Leu Arg Glu Glu Asp Ile Gly Lys Asn Arg Ala
        115                 120                 125
```

-continued

```
Glu Val Ser Gln Pro Arg Leu Ala Glu Leu Asn Ser Tyr Val Pro Val
    130                 135                 140

Thr Ala Tyr Thr Gly Pro Leu Val Glu Asp Phe Leu Ser Gly Phe Gln
145                 150                 155                 160

Val Val Val Leu Thr Asn Thr Pro Leu Glu Asp Gln Leu Arg Val Gly
                165                 170                 175

Glu Phe Cys His Asn Arg Gly Ile Lys Leu Val Val Ala Asp Thr Arg
            180                 185                 190

Gly Leu Phe Gly Gln Leu Phe Cys Asp Phe Gly Glu Glu Met Ile Leu
        195                 200                 205

Thr Asp Ser Asn Gly Glu Gln Pro Leu Ser Ala Met Val Ser Met Val
    210                 215                 220

Thr Lys Asp Asn Pro Gly Val Val Thr Cys Leu Asp Glu Ala Arg His
225                 230                 235                 240

Gly Phe Glu Ser Gly Asp Phe Val Ser Phe Ser Glu Val Gln Gly Met
                245                 250                 255

Val Glu Leu Asn Gly Asn Gln Pro Met Glu Ile Lys Val Leu Gly Pro
            260                 265                 270

Tyr Thr Phe Ser Ile Cys Asp Thr Ser Asn Phe Ser Asp Tyr Ile Arg
        275                 280                 285

Gly Gly Ile Val Ser Gln Val Lys Val Pro Lys Lys Ile Ser Phe Lys
    290                 295                 300

Ser Leu Val Ala Ser Leu Ala Glu Pro Asp Phe Val Val Thr Asp Phe
305                 310                 315                 320

Ala Lys Phe Ser Arg Pro Ala Gln Leu His Ile Gly Phe Gln Ala Leu
                325                 330                 335

His Gln Phe Cys Ala Gln His Gly Arg Pro Pro Arg Pro Arg Asn Glu
            340                 345                 350

Glu Asp Ala Ala Glu Leu Val Ala Leu Ala Gln Ala Val Asn Ala Arg
        355                 360                 365

Ala Leu Pro Ala Val Gln Gln Asn Asn Leu Asp Glu Asp Leu Ile Arg
    370                 375                 380

Lys Leu Ala Tyr Val Ala Ala Gly Asp Leu Ala Pro Ile Asn Ala Phe
385                 390                 395                 400

Ile Gly Gly Leu Ala Ala Gln Glu Val Met Lys Ala Cys Ser Gly Lys
                405                 410                 415

Phe Met Pro Ile Met Gln Trp Leu Tyr Phe Asp Ala Leu Glu Cys Leu
            420                 425                 430

Pro Glu Asp Lys Glu Val Leu Thr Glu Asp Lys Cys Leu Gln Arg Gln
        435                 440                 445

Asn Arg Tyr Asp Gly Gln Val Ala Val Phe Gly Ser Asp Leu Gln Glu
    450                 455                 460

Lys Leu Gly Lys Gln Lys Tyr Phe Leu Val Gly Ala Gly Ala Ile Gly
465                 470                 475                 480

Cys Glu Leu Leu Lys Asn Phe Ala Met Ile Gly Leu Gly Cys Gly Glu
                485                 490                 495

Gly Gly Glu Ile Ile Val Thr Asp Met Asp Thr Ile Glu Lys Ser Asn
            500                 505                 510

Leu Asn Arg Gln Phe Leu Phe Arg Pro Trp Asp Val Thr Lys Leu Lys
        515                 520                 525

Ser Asp Thr Ala Ala Ala Ala Val Arg Gln Met Asn Pro His Ile Arg
    530                 535                 540
```

-continued

```
Val Thr Ser His Gln Asn Arg Val Gly Pro Asp Thr Glu Arg Ile Tyr
545                 550                 555                 560

Asp Asp Asp Phe Phe Gln Asn Leu Asp Gly Val Ala Asn Ala Leu Asp
                565                 570                 575

Asn Val Asp Ala Arg Met Tyr Met Asp Arg Arg Cys Val Tyr Tyr Arg
            580                 585                 590

Lys Pro Leu Leu Glu Ser Gly Thr Leu Gly Thr Lys Gly Asn Val Gln
        595                 600                 605

Val Val Ile Pro Phe Leu Thr Glu Ser Tyr Ser Ser Ser Gln Asp Pro
    610                 615                 620

Pro Glu Lys Ser Ile Pro Ile Cys Thr Leu Lys Asn Phe Pro Asn Ala
625                 630                 635                 640

Ile Glu His Thr Leu Gln Trp Ala Arg Asp Glu Phe Glu Gly Leu Phe
                645                 650                 655

Lys Gln Pro Ala Glu Asn Val Asn Gln Tyr Leu Thr Asp Pro Lys Phe
            660                 665                 670

Val Glu Arg Thr Leu Arg Leu Ala Gly Thr Gln Pro Leu Glu Val Leu
        675                 680                 685

Glu Ala Val Gln Arg Ser Leu Val Leu Gln Arg Pro Gln Thr Trp Ala
    690                 695                 700

Asp Cys Val Thr Trp Ala Cys His His Trp His Thr Gln Tyr Ser Asn
705                 710                 715                 720

Asn Ile Arg Gln Leu Leu His Asn Phe Pro Pro Asp Gln Leu Thr Ser
                725                 730                 735

Ser Gly Ala Pro Phe Trp Ser Gly Pro Lys Arg Cys Pro His Pro Leu
            740                 745                 750

Thr Phe Asp Val Asn Asn Pro Leu His Leu Asp Tyr Val Met Ala Ala
        755                 760                 765

Ala Asn Leu Phe Ala Gln Thr Tyr Gly Leu Thr Gly Ser Gln Asp Arg
    770                 775                 780

Ala Ala Val Ala Thr Phe Leu Gln Ser Val Gln Val Pro Glu Phe Thr
785                 790                 795                 800

Pro Lys Ser Gly Val Lys Ile His Val Ser Asp Gln Glu Leu Gln Ser
                805                 810                 815

Ala Asn Ala Ser Val Asp Asp Ser Arg Leu Glu Glu Leu Lys Ala Thr
            820                 825                 830

Leu Pro Ser Pro Asp Lys Leu Pro Gly Phe Lys Met Tyr Pro Ile Asp
        835                 840                 845

Phe Glu Lys Asp Asp Asp Ser Asn Phe His Met Asp Phe Ile Val Ala
    850                 855                 860

Ala Ser Asn Leu Arg Ala Glu Asn Tyr Asp Ile Pro Ser Ala Asp Arg
865                 870                 875                 880

His Lys Ser Lys Leu Ile Ala Gly Lys Ile Ile Pro Ala Ile Ala Thr
                885                 890                 895

Thr Thr Ala Ala Val Val Gly Leu Val Cys Leu Glu Leu Tyr Lys Val
            900                 905                 910

Val Gln Gly His Arg Gln Leu Asp Ser Tyr Lys Asn Gly Phe Leu Asn
        915                 920                 925

Leu Ala Leu Pro Phe Phe Gly Phe Ser Glu Pro Leu Ala Ala Pro Arg
    930                 935                 940

His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu
```

-continued

```
                965                 970                 975

Asp Tyr Phe Lys Thr Glu His Lys Leu Glu Ile Thr Met Leu Ser Gln
            980                 985                 990

Gly Val Ser Met Leu Tyr Ser Phe  Phe Met Pro Ala Ala  Lys Leu Lys
        995                 1000                1005

Glu Arg  Leu Asp Gln Pro Met  Thr Glu Ile Val Ser  Arg Val Ser
    1010                1015                1020

Lys Arg  Lys Leu Gly Arg His  Val Arg Ala Leu Val  Leu Glu Leu
    1025                1030                1035

Cys Cys  Asn Asp Glu Ser Gly  Glu Asp Val Glu Val  Pro Tyr Val
    1040                1045                1050

Arg Tyr  Thr Ile Arg
    1055


<210> SEQ ID NO 5
<211> LENGTH: 154
<212> TYPE: PRT
<213> ORGANISM: Homo sapiens

<400> SEQUENCE: 5

Met Ala Ala Ser Arg Arg Leu Met Lys Glu Leu Glu Glu Ile Arg Lys
1               5                   10                  15

Cys Gly Met Lys Asn Phe Arg Asn Ile Gln Val Asp Glu Ala Asn Leu
            20                  25                  30

Leu Thr Trp Gln Gly Leu Ile Val Pro Asp Asn Pro Pro Tyr Asp Lys
        35                  40                  45

Gly Ala Phe Arg Ile Glu Ile Asn Phe Pro Ala Glu Tyr Pro Phe Lys
    50                  55                  60

Pro Pro Lys Ile Thr Phe Lys Thr Lys Ile Tyr His Pro Asn Ile Asp
65                  70                  75                  80

Glu Lys Gly Gln Val Cys Leu Pro Val Ile Ser Ala Glu Asn Trp Lys
                85                  90                  95

Pro Ala Thr Lys Thr Asp Gln Val Ile Gln Ser Leu Ile Ala Leu Val
            100                 105                 110

Asn Asp Pro Gln Pro Glu His Pro Leu Arg Ala Asp Leu Ala Glu Glu
        115                 120                 125

Tyr Ser Lys Asp Arg Lys Lys Phe Cys Lys Asn Ala Glu Glu Phe Thr
    130                 135                 140

Lys Lys Tyr Gly Glu Lys Arg Pro Val Asp
145                 150


<210> SEQ ID NO 6
<211> LENGTH: 852
<212> TYPE: PRT
<213> ORGANISM: Homo sapiens

<400> SEQUENCE: 6

Met Lys Arg Ala Ala Ala Lys His Leu Ile Glu Arg Tyr Tyr His Gln
1               5                   10                  15

Leu Thr Glu Gly Cys Gly Asn Glu Ala Cys Thr Asn Glu Phe Cys Ala
            20                  25                  30

Ser Cys Pro Thr Phe Leu Arg Met Asp Asn Asn Ala Ala Ala Ile Lys
        35                  40                  45

Ala Leu Glu Leu Tyr Lys Ile Asn Ala Lys Leu Cys Asp Pro His Pro
    50                  55                  60

Ser Lys Lys Gly Ala Ser Ser Ala Tyr Leu Glu Asn Ser Lys Gly Ala
```

-continued

```
65                  70                  75                  80

Pro Asn Asn Ser Cys Ser Glu Ile Lys Met Asn Lys Lys Gly Ala Arg
                85                  90                  95

Ile Asp Phe Lys Asp Val Thr Tyr Leu Thr Glu Glu Lys Val Tyr Glu
            100                 105                 110

Ile Leu Glu Leu Cys Arg Glu Arg Glu Asp Tyr Ser Pro Leu Ile Arg
        115                 120                 125

Val Ile Gly Arg Val Phe Ser Ser Ala Glu Ala Leu Val Gln Ser Phe
    130                 135                 140

Arg Lys Val Lys Gln His Thr Lys Glu Glu Leu Lys Ser Leu Gln Ala
145                 150                 155                 160

Lys Asp Glu Asp Lys Asp Glu Asp Glu Lys Glu Lys Ala Ala Cys Ser
                165                 170                 175

Ala Ala Ala Met Glu Glu Asp Ser Glu Ala Ser Ser Ser Arg Ile Gly
            180                 185                 190

Asp Ser Ser Gln Gly Asp Asn Asn Leu Gln Lys Leu Gly Pro Asp Asp
        195                 200                 205

Val Ser Val Asp Ile Asp Ala Ile Arg Arg Val Tyr Thr Arg Leu Leu
    210                 215                 220

Ser Asn Glu Lys Ile Glu Thr Ala Phe Leu Asn Ala Leu Val Tyr Leu
225                 230                 235                 240

Ser Pro Asn Val Glu Cys Asp Leu Thr Tyr His Asn Val Tyr Ser Arg
                245                 250                 255

Asp Pro Asn Tyr Leu Asn Leu Phe Ile Ile Val Met Glu Asn Arg Asn
            260                 265                 270

Leu His Ser Pro Glu Tyr Leu Glu Met Ala Leu Pro Leu Phe Cys Lys
        275                 280                 285

Ala Met Ser Lys Leu Pro Leu Ala Ala Gln Gly Lys Leu Ile Arg Leu
    290                 295                 300

Trp Ser Lys Tyr Asn Ala Asp Gln Ile Arg Arg Met Met Glu Thr Phe
305                 310                 315                 320

Gln Gln Leu Ile Thr Tyr Lys Val Ile Ser Asn Glu Phe Asn Ser Arg
                325                 330                 335

Asn Leu Val Asn Asp Asp Asp Ala Ile Val Ala Ala Ser Lys Cys Leu
            340                 345                 350

Lys Met Val Tyr Tyr Ala Asn Val Val Gly Gly Glu Val Asp Thr Asn
        355                 360                 365

His Asn Glu Glu Asp Asp Glu Glu Pro Ile Pro Glu Ser Ser Glu Leu
    370                 375                 380

Thr Leu Gln Glu Leu Leu Gly Glu Glu Arg Arg Asn Lys Lys Gly Pro
385                 390                 395                 400

Arg Val Asp Pro Leu Glu Thr Glu Leu Gly Val Lys Thr Leu Asp Cys
                405                 410                 415

Arg Lys Pro Leu Ile Pro Phe Glu Glu Phe Ile Asn Glu Pro Leu Asn
            420                 425                 430
```

-continued

```
Glu Val Leu Glu Met Asp Lys Asp Tyr Thr Phe Phe Lys Val Glu Thr
        435                 440                 445

Glu Asn Lys Phe Ser Phe Met Thr Cys Pro Phe Ile Leu Asn Ala Val
    450                 455                 460

Thr Lys Asn Leu Gly Leu Tyr Tyr Asp Asn Arg Ile Arg Met Tyr Ser
465                 470                 475                 480

Glu Arg Arg Ile Thr Val Leu Tyr Ser Leu Val Gln Gly Gln Gln Leu
                485                 490                 495

Asn Pro Tyr Leu Arg Leu Lys Val Arg Arg Asp His Ile Ile Asp Asp
            500                 505                 510

Ala Leu Val Arg Leu Glu Met Ile Ala Met Glu Asn Pro Ala Asp Leu
        515                 520                 525

Lys Lys Gln Leu Tyr Val Glu Phe Glu Gly Glu Gln Gly Val Asp Glu
    530                 535                 540

Gly Gly Val Ser Lys Glu Phe Phe Gln Leu Val Val Glu Glu Ile Phe
545                 550                 555                 560

Asn Pro Asp Ile Gly Met Phe Thr Tyr Asp Glu Ser Thr Lys Leu Phe
                565                 570                 575

Trp Phe Asn Pro Ser Ser Phe Glu Thr Glu Gly Gln Phe Thr Leu Ile
            580                 585                 590

Gly Ile Val Leu Gly Leu Ala Ile Tyr Asn Asn Cys Ile Leu Asp Val
        595                 600                 605

His Phe Pro Met Val Val Tyr Arg Lys Leu Met Gly Lys Lys Gly Thr
    610                 615                 620

Phe Arg Asp Leu Gly Asp Ser His Pro Val Leu Tyr Gln Ser Leu Lys
625                 630                 635                 640

Asp Leu Leu Glu Tyr Glu Gly Asn Val Glu Asp Asp Met Met Ile Thr
                645                 650                 655

Phe Gln Ile Ser Gln Thr Asp Leu Phe Gly Asn Pro Met Met Tyr Asp
            660                 665                 670

Leu Lys Glu Asn Gly Asp Lys Ile Pro Ile Thr Asn Glu Asn Arg Lys
        675                 680                 685

Glu Phe Val Asn Leu Tyr Ser Asp Tyr Ile Leu Asn Lys Ser Val Glu
    690                 695                 700

Lys Gln Phe Lys Ala Phe Arg Arg Gly Phe His Met Val Thr Asn Glu
705                 710                 715                 720

Ser Pro Leu Lys Tyr Leu Phe Arg Pro Glu Glu Ile Glu Leu Leu Ile
                725                 730                 735

Cys Gly Ser Arg Asn Leu Asp Phe Gln Ala Leu Glu Glu Thr Thr Glu
            740                 745                 750

Tyr Asp Gly Gly Tyr Thr Arg Asp Ser Val Leu Ile Arg Glu Phe Trp
        755                 760                 765

Glu Ile Val His Ser Phe Thr Asp Glu Gln Lys Arg Leu Phe Leu Gln
    770                 775                 780

Phe Thr Thr Gly Thr Asp Arg Ala Pro Val Gly Gly Leu Gly Lys Leu
785                 790                 795                 800

Lys Met Ile Ile Ala Lys Asn Gly Pro Asp Thr Glu Arg Leu Pro Thr
                805                 810                 815

Ser His Thr Cys Phe Asn Val Leu Leu Leu Pro Glu Tyr Ser Ser Lys
            820                 825                 830
```

-continued

```
Glu Lys Leu Lys Glu Arg Leu Leu Lys Ala Ile Thr Tyr Ala Lys Gly
        835                 840                 845

Phe Gly Met Leu
    850
```